United States Patent
Cady et al.

(10) Patent No.: US 11,484,528 B2
(45) Date of Patent: *Nov. 1, 2022

(54) LONG-ACTING INJECTABLE FORMULATIONS COMPRISING AN ISOXAZOLINE ACTIVE AGENT, METHODS AND USES THEREOF

(71) Applicant: BOEHRINGER INGELHEIM ANIMAL HEALTH USA INC., Duluth, GA (US)

(72) Inventors: Susan Mancini Cady, Yardley, PA (US); Peter Cheifetz, East Windor, NJ (US); Izabela Galeska, Newtown, PA (US); Loic Le Hir de Fallois, Atlanta, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 76 days.

This patent is subject to a terminal disclaimer.

(21) Appl. No.: 16/588,439

(22) Filed: Sep. 30, 2019

(65) Prior Publication Data

US 2020/0022959 A1    Jan. 23, 2020

Related U.S. Application Data

(63) Continuation of application No. 15/054,260, filed on Feb. 26, 2016, now Pat. No. 10,561,641.

(60) Provisional application No. 62/121,350, filed on Feb. 26, 2015.

(51) Int. Cl.

| A61K 31/42 | (2006.01) |
|---|---|
| A61K 9/00 | (2006.01) |
| A61K 47/10 | (2017.01) |
| A61K 31/422 | (2006.01) |
| A01P 7/04 | (2006.01) |
| A61K 31/69 | (2006.01) |
| A61K 45/06 | (2006.01) |

(52) U.S. Cl.
CPC .............. *A61K 31/42* (2013.01); *A01P 7/04* (2021.08); *A61K 9/0019* (2013.01); *A61K 31/422* (2013.01); *A61K 31/69* (2013.01); *A61K 45/06* (2013.01); *A61K 47/10* (2013.01)

(58) Field of Classification Search
CPC ........ A61K 31/42; A61K 31/69; A61K 45/06; A61K 9/0019; A61K 47/10; A61K 31/422; A61K 9/00; A01P 7/04; A01N 43/80; A61P 43/00; A61P 33/14; A61P 33/10; A61P 33/00

See application file for complete search history.

(56) References Cited

U.S. PATENT DOCUMENTS

| 8,133,918 B2 ‡ | 3/2012 | Zhang | A61K 45/06 514/73 |
|---|---|---|---|
| 8,410,153 B2 ‡ | 4/2013 | Lahm | C07D 261/04 514/378 |
| 10,561,641 B2* | 2/2020 | Cady | A61P 43/00 |
| 2005/0147680 A1 | 7/2005 | Blakely et al. | |
| 2010/0254959 A1 ‡ | 10/2010 | Lahm | C07D 261/04 424/93 |
| 2011/0245274 A1 ‡ | 10/2011 | Nanchen | A01N 43/80 514/25 |
| 2012/0232026 A1 ‡ | 9/2012 | Curtis | A01N 43/90 514/30 |
| 2013/0095126 A1 ‡ | 4/2013 | Perret | A01N 43/80 424/18 |
| 2013/0131016 A1 ‡ | 5/2013 | Akama | C07F 5/027 514/64 |
| 2013/0137735 A1 ‡ | 5/2013 | Currie | A01N 43/80 514/37 |
| 2013/0324538 A1 ‡ | 12/2013 | Gauvry | A01N 43/80 514/23 |
| 2013/0345221 A1 ‡ | 12/2013 | Gauvry | C07D 413/04 514/23 |
| 2016/0081986 A1 ‡ | 3/2016 | de Rose | A61K 47/14 514/210.18 |

FOREIGN PATENT DOCUMENTS

| CN | 101351456 A | | 2/2009 |
|---|---|---|---|
| CN | 101548945 A | ‡ | 10/2009 |
| CN | 101548945 A | | 10/2009 |
| CN | 102256971 A | | 11/2011 |
| CN | 103705452 A | ‡ | 4/2014 |
| CN | 103705452 A | | 4/2014 |
| CN | 103705453 A | ‡ | 4/2014 |

(Continued)

OTHER PUBLICATIONS

Hatefi A. et al., "Biodegradable injectable in situ forming drug delivery systems", Journal of Controlled Release, vol. 80, No. 1-3, Apr. 23, 2002, pp. 9-28.‡

Tarr, Bryan D & Yalkowsky, Samule H., "A new parenteral vehicle for the administration of some poorly water soluble anti-cancer drugs", Journal of Parenteral Science and Technology, vol. 41, No. 1, Jan.-Feb. 1987, pp. 31-33.‡

Amit Alexander, et al. "Poly(ethyleneglycol)-poly(lactic-co-glycolic acid) based thermosensitive injectable hydrogels for biomedical applications", Journal of Controlled Release, vol. 172, No. 3, Dec. 1, 2003, pp. 715-729.‡

(Continued)

*Primary Examiner* — Monica A Shin
(74) *Attorney, Agent, or Firm* — Katrina Bergbauer

(57) ABSTRACT

This invention relates to long-acting injectable formulations for combating parasites in animals, comprising at least one isoxazoline active agent, a poloxamer, and a co-solvent. This invention also provides for improved methods for eradicating, controlling, and preventing parasite infections and infestations in an animal comprising administering the long-acting injectable formulations of the invention to the animal in need thereof.

17 Claims, No Drawings

(56) References Cited

FOREIGN PATENT DOCUMENTS

| | | | | |
|---|---|---|---|---|
| CN | 103705453 A | | 4/2014 | |
| CN | 103705454 A | | 4/2014 | |
| CN | 103705454 A | ‡ | 4/2014 | |
| CN | 103705455 A | ‡ | 4/2014 | |
| CN | 103705455 A | | 4/2014 | |
| CN | 103720652 A | | 4/2014 | |
| CN | 103720652 A | ‡ | 4/2014 | |
| CN | 103768014 A | ‡ | 5/2014 | |
| CN | 103768014 A | | 5/2014 | |
| CN | 103230364 B | | 6/2014 | |
| CN | 103230364 B | ‡ | 6/2014 | |
| CN | 104334159 A | ‡ | 2/2015 | ......... B29C 37/0003 |
| CN | 104334159 A | | 2/2015 | |
| JP | 2013-508381 A | | 3/2013 | |
| JP | 2014-97982 A | | 5/2014 | |
| JP | 2014-527081 A | | 10/2014 | |
| WO | 03/017976 A1 | | 3/2003 | |
| WO | WO-03/017976 A1 | ‡ | 3/2003 | ............ A61K 9/0014 |
| WO | 2007079162 A1 | | 7/2007 | |
| WO | 2009024541 A2 | | 2/2009 | |
| WO | 2010070068 A2 | | 6/2010 | |
| WO | 2011049958 A2 | | 4/2011 | |
| WO | 2011/075591 A1 | | 6/2011 | |
| WO | WO-2011/075591 A1 | ‡ | 6/2011 | ............... C07K 5/06 |
| WO | 2013039948 A1 | ‡ | 3/2013 | |
| WO | 2013039948 A1 | | 3/2013 | |
| WO | 2013150055 A1 | | 10/2013 | |
| WO | WO-2013150055 A1 | ‡ | 10/2013 | |
| WO | 2014/039475 A1 | | 3/2014 | |
| WO | WO-2014/039475 A1 | ‡ | 3/2014 | ............. A01N 43/90 |

OTHER PUBLICATIONS

Pluronic L61 Block Copolymer Surfactant, Technical Bulletin, 2002, BASF Corporation, p. 1. (Year: 2002).‡

Pluronic L44 N INH Block Copolymer Surfactant, Technical Bulletin, 2008, BASF Corporation, p. 1. (Year: 2008).‡

Pluronic F127 Block Copolymer Surfactant, Technical Bulletin, 2012, BASF Corporation, p. 1. (Year: 2012).‡

Luo Mingsheng et al edited, "Pharmaceutical Excipients", Sichuan Science and Technology Press, publication date: Mar. 31, 1993, p. 542-543.

Luo Mingsheng et al edited, "Pharmaceutical Excipients", Sichuan Science and Technology Press, publication date Mar. 31, 1993, p. 542-543. [English Translation of Non-Patent Literature Reference No. 1].

Christian Matschke et al. "Sustained-release injectables formed in situ and their potential use for veterinary products", Journal of Controlled Release, vol. 85, 2002, pp. 1-15.

Piuronic L61 Block Copolymer Surfactant, Technical Bulletin, 2002, BASF Corporation, p. 1. (Year: 2002).

Piuronic L44 N INH Block Copolymer Surfactant, Technical Bulletin, 2008, BASF Corporation, p. 1. (Year: 2008).

Piuronic F127 Block Copolymer Surfactant, Technical Bulletin, 2012, BASF Corporation, p. 1. (Year: 2012).

\* cited by examiner
‡ imported from a related application

LONG-ACTING INJECTABLE FORMULATIONS COMPRISING AN ISOXAZOLINE ACTIVE AGENT, METHODS AND USES THEREOF

CROSS REFERENCE TO RELATED APPLICATIONS

This application is a continuation application of U.S. patent application Ser. No. 15/054,260, filed Feb. 26, 2016, which claims the benefit of U.S. Provisional Application No. 62/121,350, filed Feb. 26, 2015, both of which are incorporated herein by reference, in their entirety.

FIELD OF THE INVENTION

The present invention provides long-acting injectable formulations comprising at least one isoxazoline active agent, a block co-polymer of ethylene oxide and propylene oxide (poloxamer) and, optionally, a co-solvent; the use of these formulations against parasites (including ectoparasites (e.g., fleas or ticks) and/or endoparasites), and methods for preventing or treating parasitic infections and infestations in animals.

BACKGROUND OF THE INVENTION

Animals such as mammals and birds are often susceptible to parasite infestations/infections. These parasites may be ectoparasites, such as fleas, ticks and parasitic flies, and endoparasites such as nematodes and other worms. Domesticated animals, such as cats and dogs, are often infested with one or more of the following ectoparasites:
  fleas (e.g. *Ctenocephalides* spp., such as *Ctenocephalides felis* and the like);
  ticks (e.g. *Rhipicephalus* spp., *Ixodes* spp., *Dermacentor* spp., *Amblyomma* spp., and the like);
  mites (e.g. *Demodex* spp., *Sarcoptes* spp., *Otodectes* spp., and the like);
  lice (e.g. *Trichodectes* spp., *Cheyletiella* spp., *Linognathus* spp. and the like);
  mosquitoes (*Aedes* spp., *Culex* spp., *Anopheles* spp. and the like); and
  flies (*Haematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and psychological health of the animal or human. However, the most serious problem associated with ticks is that they are vectors of pathogenic agents in both humans and animals. Major diseases which may be transmitted by ticks include borrelioses (Lyme disease caused by *Borrelia burgdorferi*), babesiosis (or piroplasmoses caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, cattle are affected by a large number of parasites. A parasite which is prevalent among cattle in some regions are ticks of the genus *Rhipicephalus*, especially those of the species *microplus* (cattle tick), *decoloratus* and *annulatus*. Ticks such as *Rhipicephalus microplus* (formerly *Boophilus microplus*) are difficult to control because they lay eggs in the pasture where farm animals graze.

This species of ticks is considered a one-host tick and spends immature and adult stages on one animal before the female engorges and falls off the host to lay eggs in the environment. The life cycle of the tick is approximately three to four weeks. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesiosis ("cattle fever") and anaplasmosis.

Animals and humans also suffer from endoparasitic infections including, for example, helminthiasis which is caused by of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting companion animals and poultry. Other parasites which occur in the gastrointestinal tract of animals and humans include *Ancylostoma*, *Necator*, *Ascaris*, *Strongyloides*, *Trichinella*, *Capillaria*, *Toxocara*, *Toxascaris*, *Trichuris*, *Enterobius* and parasites which are found in the blood or other tissues and organs such as filarial worms and the extra intestinal stages of *Strongyloides*, *Toxocara* and *Trichinella*.

Recently, isoxazole and isoxazoline-containing compounds have been demonstrated to be effective against parasites that harm animals. For example, U.S. Pat. No. 7,964,204 (to DuPont, incorporated by reference herein in its entirety) discloses isoxazoline compounds according to Formula (I) below, which are active against ectoparasites and/or endoparasites.

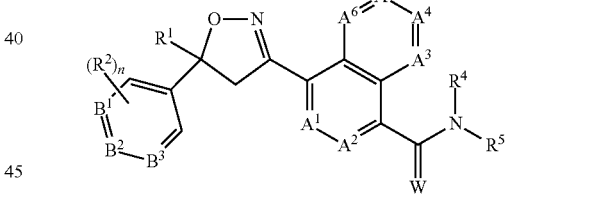

(I)

In addition, published patent application nos. US 2010/0254960 A1, WO 2007/070606 A2, WO 2007/123855 A2, WO 2010/003923 A1, U.S. Pat. Nos. 7,951,828 & 7,662,972, US 2010/0137372 A1, US 2010/0179194 A2, US 2011/0086886 A2, US 2011/0059988 A1, US 2010/0179195 A1 and WO 2007/075459 A2 and U.S. Pat. Nos. 8,410,153; 7,947,171; 8,618,126; 8,466,115; 8,383,659; 8,853,186; 7,951,828 and 7,662,972 (all incorporated herein by reference in their entirety) describe various other parasiticidal isoxazoline compounds. Other published patent applications that describe various other parasiticidal isoxazoline compounds and formulations comprising the same include WO 2007/079162 A1, WO 2008/154528 A1, WO 2009/002809 A2, WO 2011/149749 A1, WO 2013/078070, WO 2014/439475 A1, U.S. Pat. No. 8,466,115, WO 2012/120399, WO 2014/039484, WO 2014/189837, (Zoetis) and WO2012 120135A1 (Novartis). WO 2012/089623 describes topical localized isoxazoline formulations comprising glycofurol. WO 2013/039948 A1 provides for topical veterinary compositions comprising at least one isoxazoline active agent and WO 2013/119442 A1 provides for oral veterinary compositions such as a soft chew which comprising at least one isoxazoline active agent. All of the publications above are incorporated herein by reference in their entirety.

In additional to topical and oral dosage forms, it is sometimes possible to formulate active agents as long-acting formulations, depending upon, for example, the physiochemical properties of the individual active agent; these properties include, for example, solubility, bioavailability, etc. For example, U.S. Pat. Nos. 6,733,767 and 8,362,086 (both incorporated herein by reference in their entirety) provide for long acting injectable formulations comprising a bioactive substance, such as, for example, an avermectin or a milbemycin and a biological acceptable polymer.

Notwithstanding the compositions comprising isoxazoline active agents alone or in combination with other active agents described in the documents above, there is a need for veterinary compositions and methods with improved efficacy, bioavailability, and spectrum of coverage to protect animals against endoparasites and/or ectoparasites. More specifically, there is a need to develop a long-acting injectable formulation comprising an isoxazoline compound, which has good bioavailability and exhibits a reduced irritation at the injection site while still being effective against parasites (e.g., fleas and ticks) for a long duration (e.g., from three (3) to six (6) months or longer).

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention for novel and inventive long-acting injectable formulations for the treatment or prevention of parasite infections or infestations in an animal comprising an antiparasitic effective amount of at least one isoxazoline compound, a poloxamer and, optionally, a co-solvent in which the formulation does not contain a pharmaceutically acceptable polymer, as defined herein, other than a poloxamer. As used herein, the term "poloxamer" means a block copolymer of ethylene oxide and propylene oxide. Different grades, sources, and brands of block copolymers of ethylene oxide and propylene oxide may be used in the long-acting injectable formulations of the invention. Likewise, for the purposes of this application, liquid polyethylene glycols (PEGs) are considered to be a co-solvent and are not considered to be a pharmaceutically acceptable polymer In accordance with this invention, it has been discovered that the inventive formulations generally show desirable bioavailability and duration of efficacy, while causing minimal irritation at the injection site. The compositions also provide desirable safety profiles toward the warm-blooded and bird animal recipients. In addition, it has been discovered that a single administration of such formulations generally provides potent activity against one or more parasites (e.g., ectoparasites), while also tending to provide fast onset of activity, long duration of activity, and/or desirable safety profiles.

The invention encompasses uses or veterinary uses of the isoxazoline compositions for the treatment or prevention or prophylaxis of parasitic infections and infestations of animals (either wild or domesticated), including livestock and companion animals such as cats, dogs, horses, chickens, sheep, goats, pigs, turkeys and cattle, with the aim of ridding these hosts of parasites commonly encountered by such animals.

The invention also provides methods for the treatment or prevention of parasitic infections and infestations in animals, comprising administering an effective amount of long-acting injectable formulations comprising an antiparasitic effective amount of at least one isoxazoline compound together with a poloxamer and a co-solvent, wherein the formulation does not contain a pharmaceutically acceptable biodegradable polymer as defined herein. Surprisingly, it has been found that the inventive isoxazoline-containing formulations described herein exhibit superior broad spectrum efficacy against harmful parasites (e.g. ectoparasites such as fleas and ticks) more rapidly, and over a long duration compared to other injectable formulations containing isoxazoline active agents known in the art while exhibiting minimal irritation at the injection site.

This invention also provides for the use of an isoxazoline in the preparation of a long-acting injectable formulation for the treatment or prevention of an animal against parasites.

In one embodiment, the invention provides for long-acting injectable formulations comprising antiparasitic effective amounts of at least one isoxazoline of formula (I) below, in combination and a pharmaceutically or veterinary acceptable liquid carrier, where variables $A^1$, $A^2$, $A^3$, $A^4$, $A^5$, $A^6$, $B^1$, $B^2$, $B^3$, $R^1$, $R^2$, $R^4$, $R^5$, W and n are defined herein.

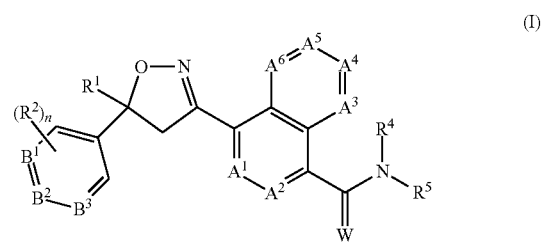

(I)

In some embodiments, the long-acting injectable formulations and methods comprise 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide as the active agent.

In other embodiments, the long-acting injectable formulations may further comprise one or more additional active agents that are systemically active. Systemically-acting active agents may include, but are not limited to, isoxazoline active agents of different structure, a systemically-acting neonicotinoid active agent, a systemically-acting 1-N-arylpyrazole active agent, macrocyclic lactones such as avermectin and milbemycin compounds, a cyclic depsipeptide such as emodepside or PF1022A or analogs thereof, benzimidazoles, imidazothiazoles, a tetrahydropyrimidine active agent, an organophosphate active agent, levamisole, a paraherquamide active agent and/or a marcfortine active agent, praziquantel, closantel, clorsulon, a spinosyn or spinosoid active agent, an amino acetonitrile active agent, an aryloazol-2-yl cyanoethyl active agent, a systemically-acting insect growth regulator. In one embodiment, the long-acting injectable formulations comprise at least one macrocyclic lactone active agent, including, but not limited to, avermectins or milbemycins. In some embodiments, the avermectin or milbemycin active agent is eprinomectin, ivermectin, selamectin, milbemectin, milbemycin D, milbemycin oxime, or moxidectin.

In other embodiments, the compositions and methods comprise at least one of thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, or an aryloazol-2-yl cyanoethylamino active agent.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

DETAILED DESCRIPTION

The present invention provides for novel and inventive long-acting injectable formulations treatment or prevention of parasite infections or infestations in an animal comprising an antiparasitic effective amount of at least one isoxazoline compound, a poloxamer and, optionally a co-solvent, wherein no other pharmaceutically acceptable polymers, as defined herein are present.

Also provided are methods and uses for the treatment and/or prophylaxis of parasitic infections and infestations of animals, comprising administering to an animal in need thereof a long-acting formulation comprising an antiparasitic effective amount of at least one isoxazoline compound, a poloxamer and, optionally a co-solvent, wherein no other pharmaceutically acceptable polymers are present.

In another embodiment, the present invention provides for long-acting injectable formulations for the treatment and/or prophylaxis of parasitic infections and infestations of animals comprising an antiparasitic effective amount of at least one isoxazoline compound and an effective amount of at least one additional systemically-acting active agent, a poloxamer and, optionally, a co-solvent wherein no other pharmaceutically acceptable polymers are present.

In a preferred embodiment of the invention, the long-acting injectable formulations comprise liquid poloxamers at room temperature (20-25° C.).

In another embodiment, the present invention provides for a long-acting injectable formulation for the treatment and/or prophylaxis of parasitic infections and infestations of animals comprising:

a) an antiparasitic effective amount of at least one isoxazoline active agent, which is:

i) an isoxazoline compound of formula (I):

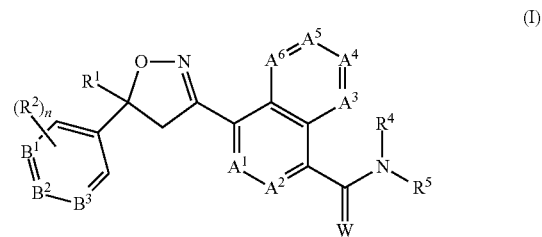

wherein:

$A^1, A^2, A^3, A^4, A^5$ and $A^6$ are independently selected from the group consisting of $CR^3$ and N, provided that at most 3 of $A^1, A^2, A^3, A^4, A^5$ and $A^6$ are N;

$B^1, B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —NO$_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —NH$_2$, —CN or —NO$_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2; or a pharmaceutically acceptable salt thereof; and/or ii) an isoxazoline compound of formula (II):

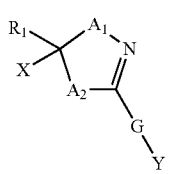

(II)

wherein:

$R_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—, —CN or —NO$_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—, —CN or —NO$_2$;

A$_1$ is oxygen; and

A$_2$ is oxygen, NR$_2$ or CR$_7$R$_8$;

G is G-1 or G-2;

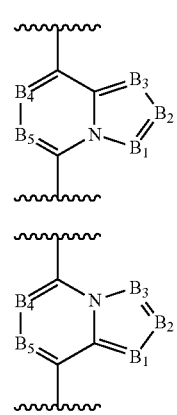

G-1

G-2

B$_1$, B$_2$, B$_3$, B$_4$ and B$_5$ are independently N or C—R$_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl) amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—, —CN or —NO$_2$; or Y is Y-1, Y-2, Y-3, Y-4, Y-5, Y-6, Y-7, Y-8, Y-9, Y-10, Y-11, Y-12 or Y-13;

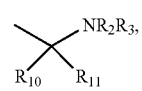

Y-1

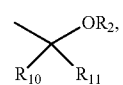

Y-2

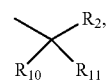

Y-3

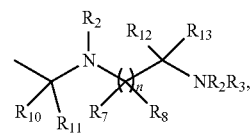

Y-4

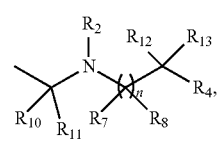

Y-5

-continued

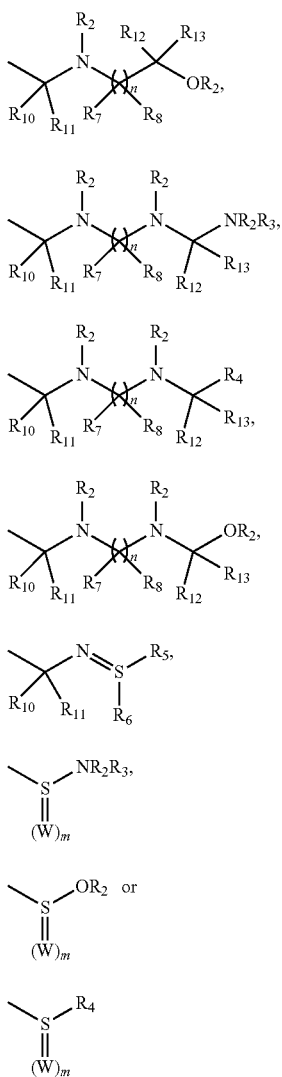

Y-6

Y-7

Y-8

Y-9

Y-10

Y-11

Y-12

Y-13

$R_2$, $R_3$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$— $R_{10}OC(O)$—;

$R_4$, $R_5$ and $R_6$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxylakyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO_2;

$R_{10}$, $R_{11}$, $R_{12}$ and $R_{13}$ are each independently hydrogen, alkyl, haloalkyl, thioalkyl, alkylthioalkyl, hydroxyalkyl, alkoxylakyl, alkenyl, haloalkenyl, alkynyl or haloalkynyl; or
$R_{10}$ together with $R_{11}$ form =O, =S or =NR_2; or
$R_{12}$ together with $R_{13}$ form =O, =S or =NR_2;
W is O, S or NR_2;
n is 1-4; and
m is 0, 1 or 2; or a pharmaceutically acceptable salt thereof; and/or iv) an isoxazoline compound of formula (III)

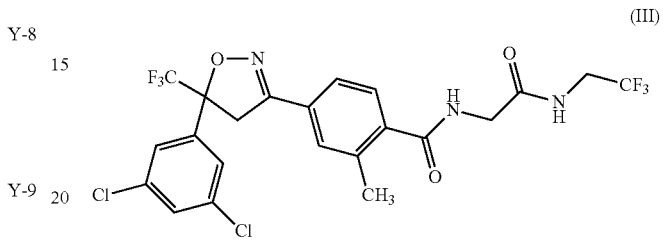

(III)

or a pharmaceutically acceptable salt thereof; and/or
iv) an isoxazoline compound of formula (IV)

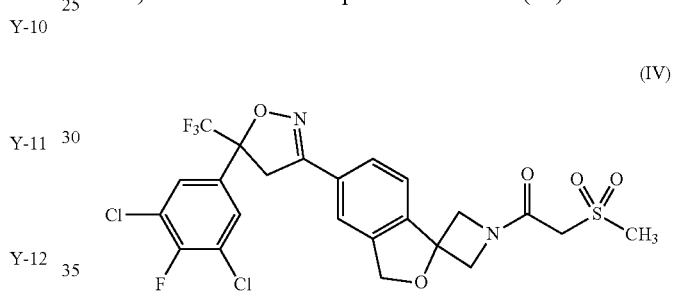

(IV)

or a pharmaceutically acceptable salt thereof; and/or
v) a isoxazoline compound of formula (V):

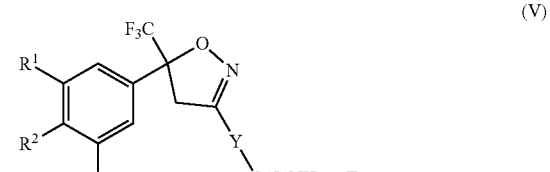

(V)

wherein $R^1$, $R^2$ and $R^3$ are independently H, Cl, F or $CF_3$;
Y is the diradical group

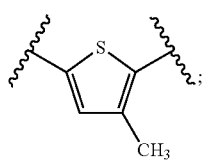

T is a $C_1$-$C_6$-alkyl group which is unsubstituted or substituted by halogen, cyano, nitro, amino, hydroxyl, $C_1$-$C_6$-alkoxy, $C_1$-$C_6$-haloalkoxy, $C_1$-$C_6$-alkylthio, $C_1$-$C_6$-alkylthio, carboxy, carbamoyl or $C_2$-$C_6$-alkanoyl group which may be unsubstituted or substituted in the alkyl portion by halogen or a pharmaceutical acceptable salt thereof; and/or vi) an isoxazoline compound of formula (VI):

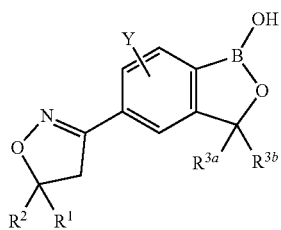

(VI)

wherein Y is hydrogen, fluoro, chloro or bromo;

$R^1$ is phenyl substituted with 2-4 substituents selected from halogen, methyl, difluoromethyl, trifluoromethyl, methoxy, trifluoromethoxy or trifluoroethoxy;

$R^2$ is methyl, fluoromethyl, trifluoromethyl or perfluoroethyl;

$R^{3a}$ and $R^{3b}$ are independently selected from hydrogen, methyl, ethyl or fluoromethyl; or $R^{3a}$ and $R^{3b}$ together combine with the carbon to which they are attached to form a cyclopentyl ring or a cyclohexyl ring; or a pharmaceutically acceptable salt thereof;

b) at least one pharmaceutically acceptable polymer which is a poloxamer;

c) optionally, at least one co-solvent;

d) optionally, an antioxidant; and e) optionally at least one pharmaceutically acceptable additive, excipient or mixtures thereof;

wherein no other pharmaceutically acceptable polymers are present.

In one embodiment, the co-solvent is a polar organic solvent that is miscible with water. In one embodiment, the co-solvent is a protic solvent such as an alcohol (e.g. ethanol or isopropanol). In another embodiment, the co-solvent is a polar aprotic solvent such as N-methylpyrrolidone, propylene carbonate, and the like. In another embodiment, the co-solvent is an organic solvent that is not miscible with water.

In another embodiment, the present invention provides for a long-acting injectable formulation for the treatment and/or prevention (prophylaxis) of parasitic infections and infestations of animals comprising:

a) an antiparasitic effective amount of at least one isoxazoline compound of formula (I):

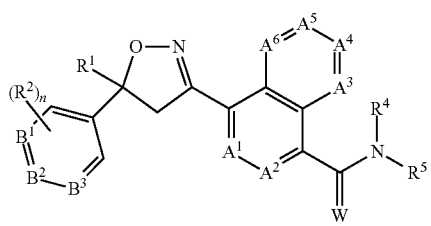

(I)

wherein:

$A^1, A^2, A^3, A^4, A^5$ and $A^6$ are independently selected from the group consisting of $CR^3$ and N, provided that at most 3 of $A^1, A^2, A^3, A^4, A^5$ and $A^6$ are N;

$B^1, B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —NO$_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —NH$_2$, —CN or —NO$_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2 or a pharmaceutically acceptable salt thereof;

b) at least one pharmaceutically acceptable polymer which is a poloxamer;

c) optionally, at least one co-solvent;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable formulation for the treatment and/or prevention (prophylaxis) of parasitic infections and infestations of animals comprising:

a) an antiparasitic effective amount of an isoxazoline compound of formula (Ia):

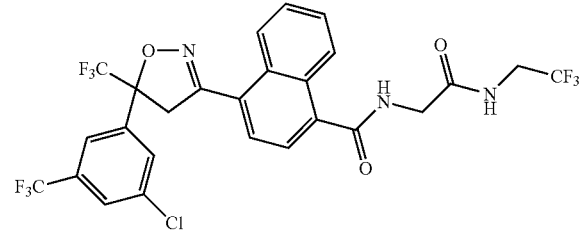

(Ia)

or a pharmaceutically acceptable salt thereof b) optionally, at least one pharmaceutically acceptable polymer which is a poloxamer;

c) optionally, at least one co-solvent;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable formulation for the treatment and/or prevention (prophylaxis) of parasitic infections and infestations of animals comprising:

a) an antiparasitic effective amount of at least one isoxazoline compound of formula (II):

(II)

wherein:

$R^1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$A_1$ is oxygen; and $A_2$ is oxygen, $NR_2$ or $CR_7R_8$;

G is G-1 or G-2;

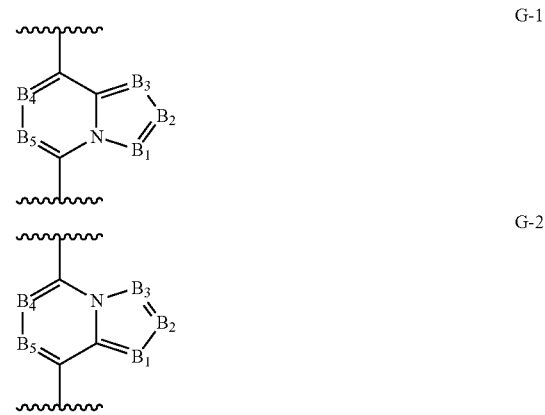

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$; or Y is Y-1, Y-2, Y-3, Y-4, Y-5, Y-6, Y-7, Y-8, Y-9, Y-10, Y-11, Y-12 or Y-13;

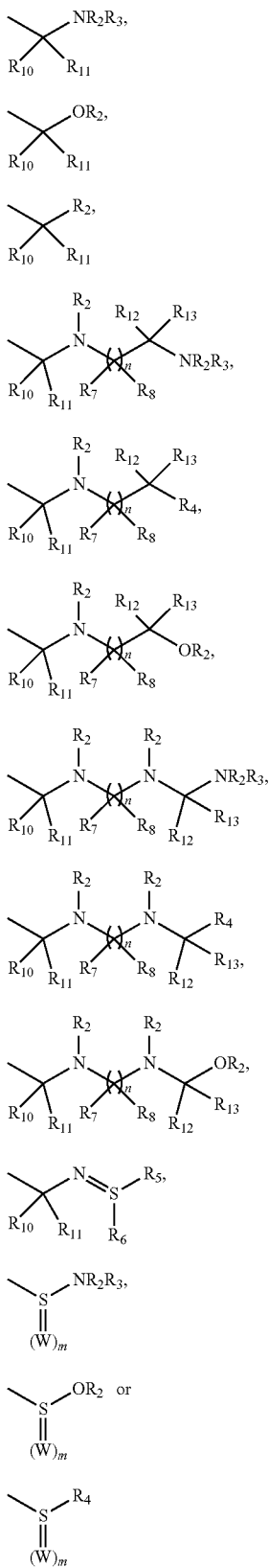

| | |
|---|---|
| Y-1 | |
| Y-2 | |
| Y-3 | |
| Y-4 | |
| Y-5 | |
| Y-6 | |
| Y-7 | |
| Y-8 | |
| Y-9 | |
| Y-10 | |
| Y-11 | |
| Y-12 | |
| Y-13 | |

$R_2$, $R_3$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$— $R_{10}OC(O)$—;

$R_4$, $R_5$ and $R_6$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxylakyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxylakyl, alkenyl, haloalkenyl, alkynyl or haloalkynyl; or $R_{10}$ together with $R_{11}$ form =O, =S or =$NR_2$; or $R_{12}$ together with $R_{13}$ form =O, =S or =$NR_2$;

W is O, S or $NR_2$;

n is 1-4; and m is 0, 1 or 2; or a pharmaceutically acceptable salt thereof;

b) at least one pharmaceutically acceptable polymer which is a poloxamer;

c) optionally, at least one co-solvent;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable formulation for the treatment and/or prevention (prophylaxis) of parasitic infections and infestations of animals comprising:

a) an antiparasitic effective amount of at least one isoxazoline compound of formulae II-1.001 to II-1.025 and 11-2.00-11-2.018:

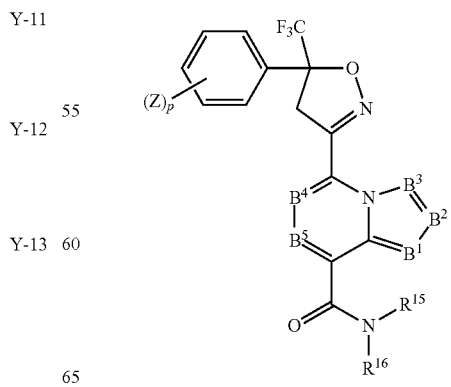

Compounds II-1.001 to II-1.025

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 1.001 | 3,5-Cl$_2$ | C—H | C—H | C—H | C—H | N | H | CH$_2$C(O)NHCH$_2$CF$_3$ |
| 1.002 | 3,5-Cl$_2$ | C—H | C—H | C—H | C—H | N | H | CH$_2$CF$_3$ |
| 1.003 | 3,5-(CF$_3$)$_2$ | C—H | C—H | C—H | C—H | N | CH$_3$ | CH$_2$CO$_2$CH$_3$ |
| 1.004 | 3,5-(CF$_3$)$_2$ | C—H | C—H | C—H | C—H | N | CH$_3$ | CH$_2$CO$_2$H |
| 1.005 | 3,5-(CF$_3$)$_2$ | C—H | C—H | C—H | C—H | N | CH$_3$ | CH$_2$C(O)NHCH$_2$CF$_3$ |
| 1.006 | 3,5-(CF$_3$)$_2$ | C—H | C—H | C—H | C—H | N | H | CH$_2$C(O)NHCH$_2$CF$_3$ |
| 1.007 | 3,5-(CF$_3$)$_2$ | C—H | C—H | C—H | C—H | N | H | CH$_2$CH$_2$SCH$_3$ |
| 1.008 | 3,5-(CF$_3$)$_2$ | C—H | C—H | C—H | C—H | C—H | H | CH$_2$C(O)NHCH$_2$CF$_3$ |
| 1.009 | 3,5-(CF$_3$)$_2$ | C—H | C—H | C—H | C—H | C—H | H | CH$_2$CH$_2$SCH$_3$ |
| 1.010 | 3,5-(CF$_3$)$_2$ | C—H | C—H | C—H | C—H | C—H | H | CH$_2$CF$_3$ |
| 1.011 | 3,5-Cl$_2$ | C—H | C—H | C—H | C—H | C—H | H | CH$_2$C(O)NHCH$_2$CF$_3$ |
| 1.012 | 3,5-Cl$_2$ | C—H | C—H | C—H | C—H | C—H | H | CH$_2$CF$_3$ |
| 1.013 | 3,5-Cl$_2$ | C—H | C—H | C—H | C—H | C—H | H | CH$_2$CH$_2$SCH$_3$ |
| 1.014 | 3-Cl,5-CF$_3$ | C—H | C—H | C—H | C—H | C—H | H | CH$_2$C(O)NHCH$_2$CF$_3$ |
| 1.015 | 3-Cl,5-CF$_3$ | C—H | C—H | C—H | C—H | C—H | H | CH$_2$CF$_3$ |
| 1.016 | 3-Cl,5-CF$_3$ | C—H | C—H | C—H | C—H | C—H | H | CH$_2$CH$_2$SCH$_3$ |
| 1.017 | 3,5-Cl$_2$ | C—H | C—H | C—Me | C—H | C—Me | H | CH$_2$C(O)NHCH$_2$CF$_3$ |
| 1.018 | 3,5-Cl$_2$ | C—H | C—H | C—Me | C—H | C—Me | H | CH$_2$CF$_3$ |
| 1.019 | 3,5-Cl$_2$ | C—H | C—H | C—Me | C—H | C—Me | H | CH$_2$CH$_2$SCH$_3$ |
| 1.020 | 3,5-(CF$_3$)$_2$ | C—H | C—H | C—Me | C—H | C—Me | H | CH$_2$C(O)NHCH$_2$CF$_3$ |
| 1.021 | 3,5-(CF$_3$)$_2$ | C—H | C—H | C—Me | C—H | C—Me | H | CH$_2$CF$_3$ |
| 1.022 | 3,5-(CF$_3$)$_2$ | C—H | C—H | C—Me | C—H | C—Me | H | CH$_2$CH$_2$SCH$_3$ |
| 1.023 | 3-Cl,5-CF$_3$ | C—H | C—H | C—Me | C—H | C—Me | H | CH$_2$C(O)NHCH$_2$CF$_3$ |
| 1.024 | 3-Cl,5-CF$_3$ | C—H | C—H | C—Me | C—H | C—Me | H | CH$_2$CF$_3$ |
| 1.025 | 3-Cl,5-CF$_3$ | C—H | C—H | C—Me | C—H | C—Me | H | CH$_2$CH$_2$SCH$_3$ |

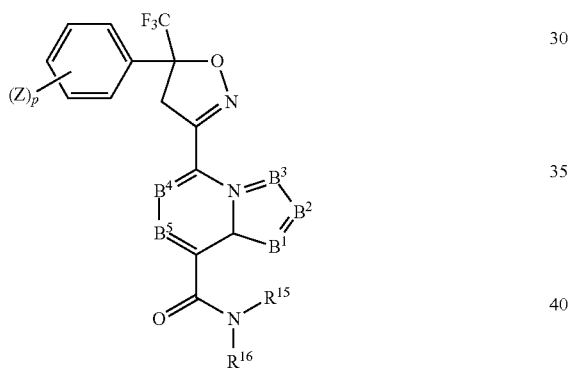

Compounds II-2.001 to II-2.018

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 2.001 | 3,5-Cl$_2$ | C—H | C—H | N | C—H | C—H | H | CH$_2$C(O)NHCH$_2$CF$_3$ |
| 2.002 | 3,5-Cl$_2$ | C—H | C—H | N | C—H | C—H | H | CH$_2$CF$_3$ |
| 2.003 | 3,5-Cl$_2$ | C—H | C—H | N | C—H | C—H | H | CH$_2$CH$_2$SCH$_3$ |
| 2.004 | 3,5-(CF$_3$)$_2$ | C—H | C—H | N | C—H | C—H | H | CH$_2$C(O)NHCH$_2$CF$_3$ |
| 2.005 | 3,5-(CF$_3$)$_2$ | C—H | C—H | N | C—H | C—H | H | CH$_2$CF$_3$ |
| 2.006 | 3,5-(CF$_3$)$_2$ | C—H | C—H | N | C—H | C—H | H | CH$_2$CH$_2$SCH$_3$ |
| 2.007 | 3-Cl,5-CF$_3$ | C—H | C—H | N | C—H | C—H | H | CH$_2$C(O)NHCH$_2$CF$_3$ |
| 2.008 | 3-Cl,5-CF$_3$ | C—H | C—H | N | C—H | C—H | H | CH$_2$CF$_3$ |
| 2.009 | 3-Cl,5-CF$_3$ | C—H | C—H | N | C—H | C—H | H | CH$_2$CH$_2$SCH$_3$ |
| 2.010 | 3,5-Cl$_2$ | C—H | C—H | C—H | C—H | C—H | H | CH$_2$C(O)NHCH$_2$CF$_3$ |
| 2.011 | 3,5-Cl$_2$ | C—H | C—H | C—H | C—H | C—H | H | CH$_2$CF$_3$ |
| 2.012 | 3,5-Cl$_2$ | C—H | C—H | C—H | C—H | C—H | H | CH$_2$CH$_2$SCH$_3$ |
| 2.013 | 3,5-(CF$_3$)$_2$ | C—H | C—H | C—H | C—H | C—H | H | CH$_2$C(O)NHCH$_2$CF$_3$ |
| 2.014 | 3,5-(CF$_3$)$_2$ | C—H | C—H | C—H | C—H | C—H | H | CH$_2$CF$_3$ |
| 2.015 | 3,5-(CF$_3$)$_2$ | C—H | C—H | C—H | C—H | C—H | H | CH$_2$CH$_2$SCH$_3$ |
| 2.016 | 3-Cl,5-CF$_3$ | C—H | C—H | C—H | C—H | C—H | H | CH$_2$C(O)NHCH$_2$CF$_3$ |
| 2.017 | 3-Cl,5-CF$_3$ | C—H | C—H | C—H | C—H | C—H | H | CH$_2$CF$_3$ |
| 2.018 | 3-Cl,5-CF$_3$ | C—H | C—H | C—H | C—H | C—H | H | CH$_2$CH$_2$SCH$_3$ | or a pharmaceutically acceptable salt thereof;
b) at least one pharmaceutically acceptable polymer which is a poloxamer;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable formulation for the treatment and/or prevention (prophylaxis) of parasitic infections and infestations of animals comprising:
a) an antiparasitic effective amount of e isoxazoline compound of formula (III)

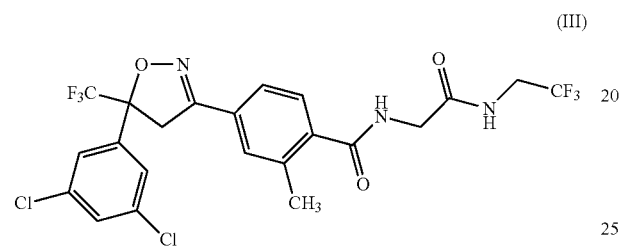

(III)

or a pharmaceutically acceptable salt thereof;
b) at least one pharmaceutically acceptable polymer which is a poloxamer;
c) optionally at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable formulation for the treatment and/or prevention (prophylaxis) of parasitic infections and infestations of animals comprising:
iv) an antiparasitic effective amount of an isoxazoline compound of formula (IV)

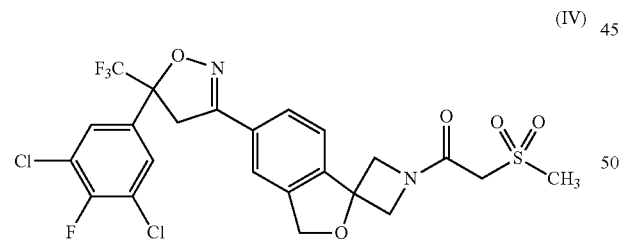

(IV)

or a pharmaceutically acceptable salt thereof; b) at least one pharmaceutically acceptable polymer which is a poloxamer;
c) optionally at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable formulation for the treatment and/or prevention (prophylaxis) of parasitic infections and infestations of animals comprising:

a) an antiparasitic effective amount of at least one isoxazoline compound of formula (V):

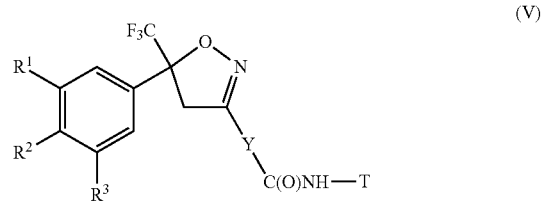

(V)

wherein $R^1$, $R^2$ and $R^3$ are independently H, $C_1$, F or $CF_3$;
Y is the diradical group

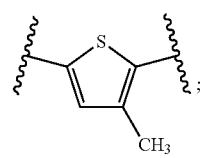

;

and
T is a $C_1$-$C_6$-alkyl group which is unsubstituted or substituted by halogen, cyano, nitro, amino, hydroxyl, $C_1$-$C_6$-alkoxy, $C_1$-$C_6$-haloalkoxy, $C_1$-$C_6$-alkylthio, $C_1$-$C_6$-alkylthio, carboxy, carbamoyl or $C_2$-$C_6$-alkanoyl group which may be unsubstituted or substituted in the alkyl portion by halogen or a pharmaceutical acceptable salt thereof
b) at least one pharmaceutically acceptable polymer which is a poloxamer;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable formulation for the treatment and/or prevention (prophylaxis) of parasitic infections and infestations of animals comprising
a) an antiparasitic effective amount of an isoxazoline compound of formula (Va):

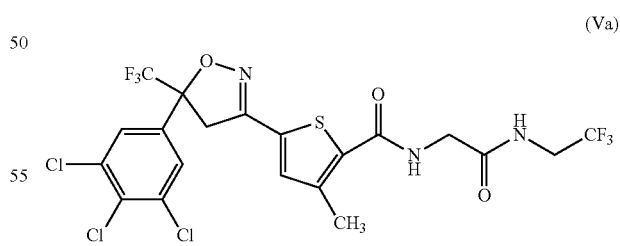

(Va)

b) at least one pharmaceutically acceptable polymer which is a poloxamer;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable formulation for the treatment and/or prevention (prophylaxis) of parasitic infections and infestations of animals comprising a) an antiparasitic effective amount of at least one compound of formula (VI):

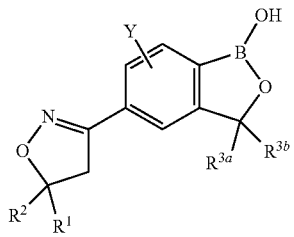

(VI)

wherein
Y is hydrogen, fluoro, chloro or bromo;
$R^1$ is phenyl substituted with 2-4 substituents selected from halogen, methyl, difluoromethyl, trifluoromethyl, methoxy, trifluoromethoxy or trifluoroethoxy;
$R^2$ is methyl, fluoromethyl, trifluoromethyl or perfluoroethyl;
$R^{3a}$ and $R^{3b}$ are independently selected from hydrogen, methyl, ethyl or fluoromethyl; or $R^{3a}$ and $R^{3b}$ together combine with the carbon to which they are attached to form a cyclopentyl ring or a cyclohexyl ring; or a pharmaceutically acceptable salt thereof
b) at least one pharmaceutically acceptable polymer which is a poloxamer;
c) optionally at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable formulation for the treatment and/or prevention (prophylaxis) of parasitic infections and infestations of animals comprising:

a) an antiparasitic effective amount of at least one compound of formula (VIa):

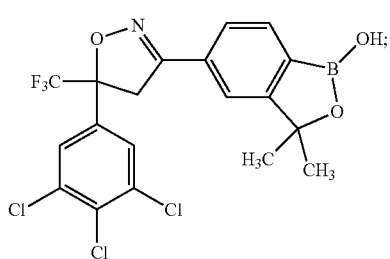

(VIa)

b) at least one pharmaceutically acceptable polymer which is a poloxamer;
c) optionally at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the long-acting injectable formulations of present invention comprise an antiparasitic effective amount of at least one isoxazoline of Formula (I), which has the formula (Ib):

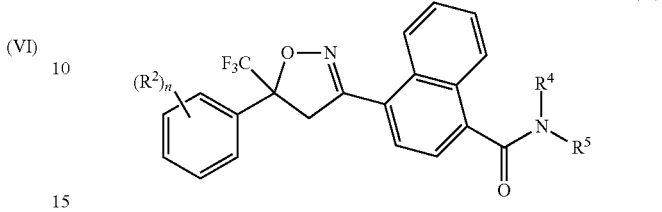

(Ib)

or a pharmaceutically acceptable salt thereof
wherein
$R^2$ independently is halogen, $C_1$-$C_6$ alkyl or $C_1$-$C_6$ haloalkyl
$R^4$ is H or $C_1$-$C_6$ alkyl;
$R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl (e.g., —$CH_2C(O)NHCH_2CF_3$); and
n is 0, 1 or 2.

In another embodiment, the long-acting injectable formulations of present invention comprise an antiparasitic effective amount of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula Ia).

The compounds of formula (I) through formula (VIa) can exist as stereoisomers where there is a chiral center and these individual stereoisomers are encompassed by the structural formulas depicted herein. Hence, in an another embodiment, the long-acting injectable formulations of present invention comprise an antiparasitic effective amount of at least one isoxazoline of Formula (I), Formula (Ia), Formula (II), Formula (II-1.1001) to Formula (II-1.025), Formula (II-2.001) to Formula (II-018), Formula (III), Formula (IV), Formula (V), Formula (Va), Formula (VI) or Formula (VIa) which is enriched in one enantiomer, or a pharmaceutically acceptable salt thereof. In an embodiment, the compounds of formula (I) to formula (VIa) present in the compositions of the invention are enriched in one enantiomer (either (S)- or (R)-configuration) in a weight:weight ratio of at least 1.5, at least 2, at least 5 or at least 10. In another embodiment, the compounds of formula (I) to formula (VIa) present in the compositions of the invention are essentially pure enantiomers.

Processes to prepare individual stereoisomers of the compounds of formula (I) through formula (VIa) (e.g., the stereoisomers for formula I-1a and formula I-1b below) from a racemic mixture comprising the same are well with the skill level of one of ordinary skill in this art.

Processes include, for example, recrystallization or chiral chromatography using, for example a Chiralpak® AD column, and processes to prepare individual stereoisomers of an isoxazoline compound are found in the prior art (see, e.g., WO 2014/090918 A1, WO 2011/104089 A1 or US 2010/0254959 A1).

The various stereoisomers include enantiomers, diastereomers and atopisomers. One of skill in the art will understand that one stereoisomer may be more active and/or may exhibit beneficial properties in when enriched relative to the other enantiomer. In addition, the skilled person in the art knows how to separate, enrich, and/or selectively prepare a stereoisomer of the isoxazoline compounds described herein. The isoxazoline compounds of formula (I) to formula (VIa) described herein contain a chiral quaternary carbon atom in the five-membered isoxazoline ring (shown by the asterisk (*); therefore, the compounds will contain at least two possible stereoisomers (e.g. enantiomers). As an example for the compounds of formula (Ia), the two possible stereoisomers resulting from the quaternary carbon are shown as formula (S)-Ia and (R)-Ia:

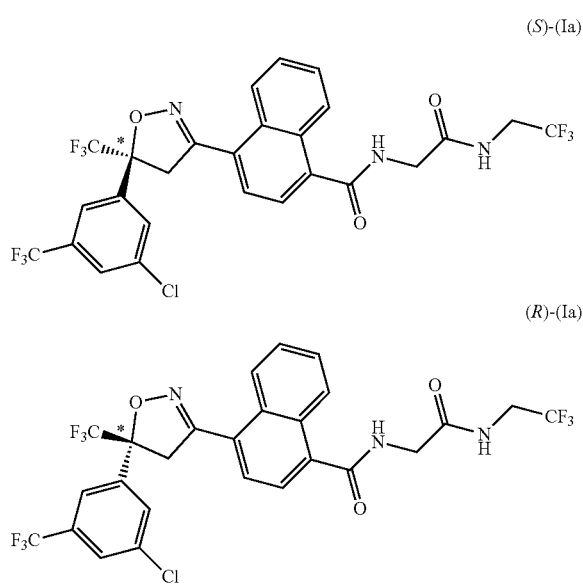

The compound of formula (S)-Ia above has the (S) configuration at the chiral carbon atom in the isoxazoline ring and the compound of formula (R)-Ia has the (R) configuration at the chiral carbon in the ring.

In one embodiment, the composition of the invention comprises a compound of formula (I), (Ia) or (Ib) that is substantially enriched in an enantiomer. By the term substantially enriched is meant wherein the weight:weight ratio is at least about 1.5 to 1 or higher in favor of the desired enantiomer In another embodiment, the long-acting injectable compositions of the invention comprise a compound of formula (I), (Ia) or (Ib) that is substantially enriched in the (S)-enantiomer. In another embodiment, the long-acting injectable compositions of the invention comprise a compound of formula (I), (Ia) or (Ib) that is substantially enriched in the (R)-enantiomer.

In another embodiment of the invention, the compositions comprise a compound of formula (I), (Ia) or (Ib) that is enriched in the (S)-enantiomer in a weight:weight ratio of at least approximately 2 to 1, (S)-enantiomer to (R)-enantiomer, or greater. In yet another embodiment, the compositions of the invention comprise a compound of formula (I), (Ia) or (Ib) that is enriched in the (S)-enantiomer in a weight:weight ratio of at least about 5 to 1, (S)-enantiomer to (R)-enantiomer, or greater. In still another embodiment, the compositions of the invention comprise a compound of formula (I), (Ia) or (Ib) that is enriched in the (S)-enantiomer in a weight:weight ratio of at least approximately 10 to 1, (S)-enantiomer to (R)-enantiomer, or greater. In still another embodiment, the compositions of the invention comprise a compound of formula (I), (Ia) or (Ib) that is essentially the pure (S)-enantiomer.

In another embodiment of the invention, the compositions comprise a compound of formula (I), (Ia) or (Ib) that is enriched in the (R)-enantiomer in a weight:weight ratio is at least approximately 2 to 1, (R)-enantiomer to (S)-enantiomer, or greater. In yet another embodiment, the compositions of the invention comprise a compound of formula (I), (Ia) or (Ib) that is enriched in the (R)-enantiomer in a weight:weight ratio of at least about 5 to 1, (R)-enantiomer to (S)-enantiomer, or greater. In still another embodiment, the compositions of the invention comprise a compound of formula (I), (Ia) or (Ib) that is enriched in the (R)-enantiomer in a weight:weight ratio of at least about 10 to 1, (R)-enantiomer to (S)-enantiomer, or greater. In still another embodiment, the compositions of the invention comprise a compound of formula (I), (Ia) or (Ib) that is essentially the pure (R)-enantiomer.

Molecular depictions drawn herein follow standard conventions for depicting stereochemistry. To indicate stereo configuration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereo configuration is intended to be specified.

In one embodiment of the invention, the more biologically active enantiomer is believed to be Formula I-1a. Formula I-1a has the (S) configuration at the chiral carbon of the isoxazoline ring and Formula I-1b has the (R) configuration at the chiral carbon. Similarly, the more biologically active enantiomers of isoxazoline compounds of formula (II) to (VIa) are believed to have the (S)-configuration at the chiral carbon of the isoxazoline ring. In certain embodiments, an isoxazoline compound of the invention or compositions comprising the compound which are enriched in an enantiomer that displays significant in vitro and in vivo activity (the eutomer) with a favorable toxicity profile whereas a compound or composition enriched with the other corresponding enantiomer displays significantly far less in vitro and in vivo activity (the distomer).

This invention comprises racemic mixtures, for example, equal amounts of the enantiomers of isoxazoline compounds of Formulae (I) to (VIa). The invention includes compounds of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (Via) that are enriched in one enantiomer compared to the racemic mixture. Also included are the essentially pure enantiomers of the compounds of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (VIa).

When enantiomerically enriched, one enantiomer is present in greater amounts than the other, and the extent of enrichment may be defined by an expression of enantiomeric excess ("ee"), which is defined as $(2x-1)\cdot 100\%$, where x is the mole fraction of the dominant enantiomer in the mixture (e.g., an ee of 20% corresponds to a 60:40 ratio of enantiomers). In some embodiments, the compositions of the invention comprise compounds that have at least a 50% enantiomeric excess. In other embodiments, the compositions of the invention comprise compounds that have at least a 75% enantiomeric excess, at least a 90% enantiomeric excess, or at least a 94% enantiomeric excess of the more active isomer. Of particular note are enantiomerically pure embodiments of the more active isomer (the eutomer).

Compounds of this invention can exist as one or more conformational isomers due to restricted rotation about the amide bond bonded to the aryl or heteroaryl ring (e.g. the amide bonded to the naphthyl group in Formula (I)). This invention comprises mixtures of conformational isomers. In addition, this invention includes compounds that are enriched in one conformer relative to others.

It will be appreciated that in addition to the compounds of formula (Ia), the other isoxazoline compounds of Formula (I), Formula (Ib), Formula (II), Formula (II-1.1001) to Formula (II-1.025), Formula (II-2.001) to Formula (II-018), Formula (III), Formula (IV), Formula (V), Formula (Va), Formula (VI) and Formula (VIa) will also have at least two possible enantiomers as a result of the quaternary carbon atom on the isoxazoline ring. In addition, certain compounds may include other chiral centers in one or more substituents.

In one embodiment, the composition of the invention comprises a compound of formula (Ia) that is substantially enriched in an enantiomer. By the term substantially enriched is meant wherein the weight:weight ratio is at least approximately 1.5 to 1 or higher in favor of the desired enantiomer. In another embodiment, the long-acting injectable compositions of the invention comprise a compound of formula (Ia) that is substantially enriched in the (S)-enantiomer. In another embodiment, the long-acting injectable compositions of the invention comprise a compound of formula (Ia) that is substantially enriched in the (R)-enantiomer.

Accordingly, in one embodiment of the invention, the compositions comprise a compound of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (VIa) that is enriched in the (S)-enantiomer in a weight:weight ratio of at least approximately 2 to 1, (S)-enantiomer to (R)-enantiomer, or greater. In yet another embodiment, the compositions of the invention comprise a compound of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (VIa), that is enriched in the (S)-enantiomer in a weight:weight ratio of at least about 5 to 1, (S)-enantiomer to (R)-enantiomer, or greater. In still another embodiment, the compositions of the invention comprise a compound of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (VIa), that is enriched in the (S)-enantiomer in a weight:weight ratio of at least approximately 10 to 1, (S)-enantiomer to (R)-enantiomer, or greater. In still another embodiment, the compositions of the invention comprise a compound of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (VIa), that is essentially the pure (S)-enantiomer.

In another embodiment of the invention, the compositions comprise a compound of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (VIa), that is enriched in the (R)-enantiomer in a weight:weight ratio is at least approximately 2 to 1, (R)-enantiomer to (S)-enantiomer, or greater. In yet another embodiment, the compositions of the invention comprise a compound of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (VIa), that is enriched in the (R)-enantiomer in a weight:weight ratio of at least about 5 to 1, (R)-enantiomer to (S)-enantiomer, or greater. In still another embodiment, the compositions of the invention comprise a compound of Formula (I), Formula (Ia), Formula (Ib), Formula (II), Formula (II-1.1001) to Formula (II-1.025), Formula (II-2.001) to Formula (II-018), Formula (III), Formula (IV), Formula (V), Formula (Va), Formula (VI) or Formula (VIa), that is enriched in the (R)-enantiomer in a weight:weight ratio of at least approximately 10 to 1, (R)-enantiomer to (S)-enantiomer, or greater. In still another embodiment, the compositions of the invention comprise a compound of Formula (I), Formula (II), Formula (II-1.1001) to Formula (II-1.025), Formula (II-2.001) to Formula (II-018), Formula (III), Formula (IV), Formula (V), Formula (Va), Formula (VI) or Formula (VIa), that is essentially the pure (R)-enantiomer.

In another embodiment, the long-acting injectable formulations of present invention comprise an antiparasitic effective amount of at least one isoxazoline disclosed in U.S. Pat. No. 7,964,204, US 2010/0254960 A1, US2011/0159107, US2012/0309620, US2012/0030841, US2010/0069247, WO 2007/125984, WO 2012/086462, U.S. Pat. Nos. 8,318,757, 8,466,115, 8,618,126, 8,822,466, 8,383,659, 8,853,186, US 2011/0144349, U.S. Pat. No. 8,053,452; US 2010/0137612, US 2010/0254959, US 2011/152081, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. Nos. 7,951,828 & 7,662,972, US 2010/0137372 A1, US 2010/0179194 A2, US 2011/0086886 A2, US 2011/0059988 A1, US 2010/0179195 A1, U.S. Pat. Nos. 7,897,630, and 7,951,828, all of which are incorporated herein by reference in their entirety.

In yet another embodiment, the long-acting injectable formulations of present invention comprise an antiparasitic effective amount of at least one isoxazoline compound described in WO 2009/02451A2 and WO 2011/075591A1, both incorporated herein by reference in their entirety.

In one embodiment, the compositions of the invention may comprise about 1 to about 50% (w/v) of an isoxazoline active agent. In another embodiment, the compositions comprise about 5 to about 50% (w/v) of an isoxazoline active agent. In another embodiment, the compositions of the invention comprise about 5 to about 40% (w/v) or about 5 to about 30% (w/v) of an isoxazoline active agent. In yet another embodiment, the compositions of the invention comprise about 5 to about 20% (w/v) of an isoxazoline active agent. In another embodiment, the compositions may comprise about 10 to about 50% (w/v) of an isoxazoline active agent. In another embodiment, the compositions may comprise about 10 to about 40% (w/v) of an isoxazoline active agent. In yet another embodiment, the compositions of the invention may comprise about 15% to about 40% (w/v), about 10% to about 35% (w/v) or about 15% to about 30% (w/v) of an isoxazoline compound.

In one embodiment, the compositions of the invention may comprise about 1% to about 70% (w/v) of a co-solvent or a mixture of co-solvents. In another embodiment, the compositions of the invention may comprise from about 1% to about 60% (w/v) of a co-solvent or a mixture of co-solvents. In another embodiment, the compositions of the invention may comprise about 1% to about 50% (w/v) of a co-solvent or a mixture of co-solvents. In still another embodiment, the compositions may comprise about 5% to about 50% (w/v), about 5% to about 40% (w/v) or about 5% to about 35% (w/v) of a co-solvent or a mixture of co-solvents.

In another embodiment, the compositions of the invention may comprise about 0.01% to about 10% (w/v) of a pharmaceutically acceptable additive, excipient or mixtures thereof. In other embodiments, the compositions may comprise about 0.01% to about 5% (w/v), about 0.1% to about 10% (w/v) or about 0.1% to about 5% (w/v) of a pharmaceutically acceptable additive, excipient or mixtures thereof.

In another embodiment, the compositions of the invention may comprise about 0.01% to about 3% (w/v) of an antioxidant. In other embodiments, the compositions may comprise about 0.01% to about 2% (w/v) of an antioxidant.

In certain embodiments the present invention provides for long-acting injectable formulations for the treatment and/or prevention of parasitic infections and infestations of animals comprising:

a) about 15 to 30% (w/v) of an isoxazoline active agent, such as, for example, any of the isoxazoline compounds provided for in the embodiments above (e.g., a compound of Formula I-VIa);

b) pharmaceutically acceptable polymer which is a poloxamer;

c) optionally, about 5% to 70% (w/v) of co-solvent or a mixture of co-solvents, which is a polar solvent miscible in water;

d) optionally, about 0.01% to about 2.0% (w/v) of an antioxidant; and e) optionally about 0.01% to about 5.0% (w/v) of a pharmaceutically acceptable additive, excipient or mixtures thereof wherein the only pharmaceutically acceptable polymer present in said long-acting injectable composition is a poloxamer and wherein the poloxamer is present in the overall composition in a proportion representing the complement to 100% of the composition.

In certain embodiments the present invention provides for long-acting injectable formulations for the treatment and/or prophylaxis of parasitic infections and infestations of animals comprising:

a) about 10 to 30% (w/v) of an isoxazoline active agent, such as, for example, any of the isoxazoline compounds provided for in the embodiments above (e.g., a compound of Formulae I-VIa), such as, a compound of the formula:

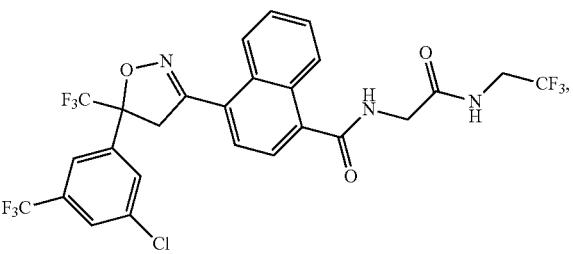
(Ia)

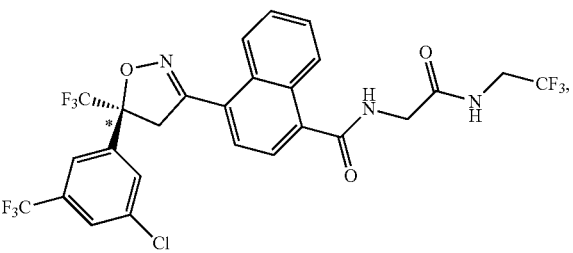
(S)-(Ia)

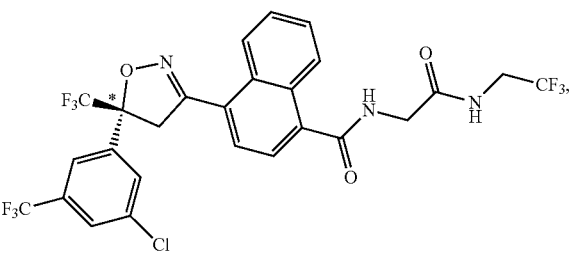
(R)-(Ia)

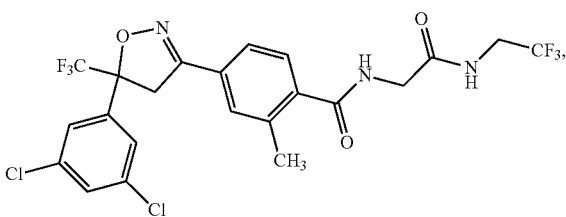
(III)

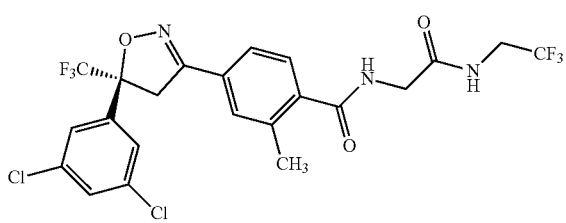
(S)-(III)

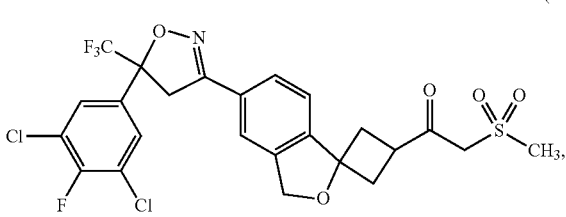
(IV)

-continued

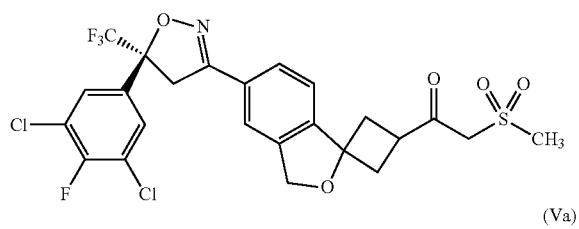
(S)-(IV)

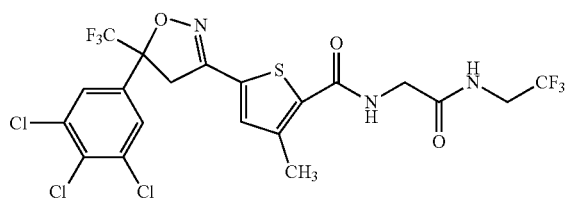
(Va)

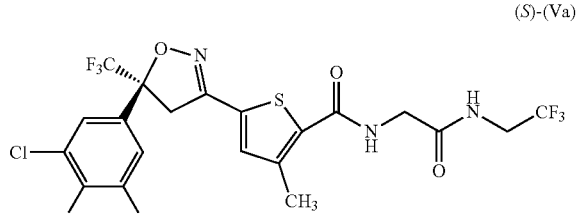
(S)-(Va)

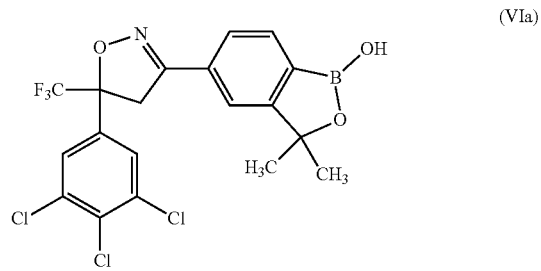 [SMILES: CC1(C)OB(O)c2ccc(C3=NOC(c4cc(Cl)c(Cl)c(Cl)c4)(C(F)(F)F)C3)cc21]
(VIa)

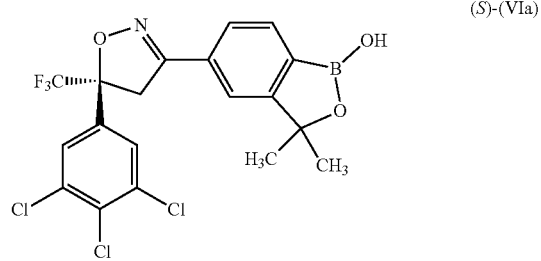
(S)-(VIa)

or a pharmaceutically acceptable salt thereof, b) pharmaceutically acceptable polymer which is a poloxamer;

c) optionally, about 5% to about 70% (w/v) of co-solvent selected from the group consisting of ethanol, isopropanol, a liquid polyethylene glycol (e.g., PEG 400), or a mixture of any of the foregoing;

d) optionally, about 0.01% to about 2.0% (w/v) of an antioxidant; and e) optionally about 0.01% to about 5.0% (w/v) of a pharmaceutically acceptable additive, excipient or mixtures thereof;

wherein the only pharmaceutically acceptable polymer present in said long-acting injectable composition is a poloxamer and wherein the poloxamer is present in the overall composition in a proportion representing the complement to 100% of the composition.

Another embodiment of the present invention is a long-acting injectable formulation for the treatment and/or prevention of parasitic infections and infestations of animals consisting essentially of:

a) an antiparasitic effective amount of at least one isoxazoline active agent, such as, for example, any of the isoxazoline compounds provided for in the embodiments above (e.g., a compound of Formulae I-VIa), and optionally at least one additionally active agent as identified in this application;

b) a poloxamer;

c) optionally, at least one co-solvent wherein said co-solvent is a polar solvent miscible in water;

d) optionally, an antioxidant; and e) optionally, at least one pharmaceutically acceptable additive, excipient or mixtures thereof.

Another embodiment of the present invention is a long-acting injectable formulation for the treatment and/or prevention of parasitic infections and infestations of animals consisting of:

a) an antiparasitic effective amount of at least one isoxazoline active agent, such as, for example, any of the isoxazoline compounds provided for in the embodiments above (e.g., a compound of Formulae I-VIa), and optionally at least one additionally active agent as identified in this application;

b) a poloxamer;

c) at least one co-solvent wherein said co-solvent is a polar solvent miscible in water;

d) optionally, an antioxidant; and e) optionally, at least one pharmaceutically acceptable additive, excipient or mixtures thereof.

In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. The term "consisting of" excludes any element, step or ingredient not specified in the claims.

DEFINITIONS

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

The term "essentially pure" is used herein to indicate that a compound or an enantiomer is at least about 90% pure, at least about 95%, at least about 98% pure, or higher.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl", which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH—CH_2O—$, $(CH_3)_3CO—$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-S(O)$_2$—, wherein alkyl is as defined above. Similarly, the term "haloalkylsulfonyl" refers to haloalkyl-S(O)$_2$— where haloalkyl is as defined above.

The term alkylamino and dialkylamino refer to alkyl-NH— and (alkyl)$_2$N— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl" refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl," "haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl) amino, or trialkylsilyl.

The terms "aralkyl" or "arylalkyl" refers to an aryl group that is bonded to the parent compound through a diradical alkylene bridge, $(—CH_2—)_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl ($—CH_2C_1$), dichloromethyl ($—CHCl_2$), trichloromethyl ($—CCl_3$)).

By the term "enriched" is meant when the weight:weight ratio is at least approximately 1.05 or higher in favor of the enantiomer that displays significant in vitro and in vivo activity (the eutomer).

Stereoisomers and Polymorphic Forms

As noted above, it will be appreciated by those of skill in the art that certain compounds within the compositions of the invention may exist and be isolated as optically active and racemic forms. Compounds having one or more chiral centers as those of formula (I) to formula (VIa) above, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses compositions comprising the specific enantiomers or diastereomers of each compound as well as mixtures of different enantiomers and/or diastereomers of the compounds of the invention that possess the useful properties described herein. In addition, the invention encompasses compositions comprising one or more conformational isomers (e.g. rotamers) as well as mixtures of conformational isomers. Conformational isomers of the isoxazoline compounds may be produced by a restriction of rotation about the amide bond bonded to the aryl or heteroaryl ring (e.g. the amide bonded to the naphthyl group in Formula (I)). The optically active forms can be prepared by, for example, resolution of the racemic forms by selective crystallization techniques, by synthesis from optically active precursors, by chiral synthesis, by chromatographic separation using a chiral stationary phase or by enzymatic resolution.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents. In some embodiments, the compositions of the invention may include up to 15% (w/w), up to 20% (w/w), or up to 30% (w/w) of a particular solid form.

Salts

Also contemplated within the scope of the invention are acid or base salts, where applicable, of the compounds of the invention provided for herein.

The term "acid salt" contemplates salts of the compounds with all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, ca-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base salt" contemplates salts of the compounds with all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4+$), alkyl- and dialkylammonium salts, and salts of cyclic amines such as the morpholine and piperidine salts.

In another embodiment, the long-acting injectable formulations of present invention comprise an effective amount of at least one isoxazoline or a pharmaceutically acceptable salt thereof in combination at least one other active agent. In one embodiment, the long-acting injectable compositions comprise an effective amount of at least one isoxazoline compound of formula (I) to (VIa), or a pharmaceutically acceptable salt thereof, in combination with at least one other active agent that is systemically-active.

Additional veterinary/pharmaceutical active ingredients may be used with the compositions of the invention. In some embodiments, the additional active agents may include, but are not limited to, acaricides, anthelmintics, anti-parasitics and insecticides. Anti-parasitic agents can include both ectoparasiticidal and/or endoparasiticidal agents.

Veterinary pharmaceutical agents that may be included in the compositions of the invention are well-known in the art (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/− clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium, calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, Propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodium thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, known in the art may be combined with the isoxazoline compounds in the long-acting injectable compositions of the invention. Examples of such phenylpyrazoles compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.).

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins and avermectin analogs such as abamectin, dimadectin, doramectin, emamectin, eprinomectin, ivermectin, latidectin, lepimectin, selamectin and ML-1,694,554, and milbemycins and milbemycin analogs such as milbemectin, milbemycin D, milbemycin oxime, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998, 131 (all incorporated herein by reference—each assigned to Merial, Ltd., Duluth, Ga.).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" $12^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment of the invention, the invention comprises a long-acting injectable formulation comprising an isoxazoline compound in combination with systemically-acting compounds from a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U. K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3 (2H)-one.

In an embodiment, the long-acting injectable formulations of present invention comprise an effective amount of at least one isoxazoline of Formula (I) to (VIa), or a pharmaceutically acceptable salt thereof, in combination with methoprene or pyriproxyfen.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoro-ethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the long-acting formulations of the present invention. These include pyrethrins (which include cinerin I, cinerin II, jasmolin I, jasmolin II, pyrethrin I, pyrethrin II and mixtures thereof) and pyrethroids, and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox. In one embodiment, the compositions can include permethrin in combination with an isoxazoline active agent.

In some embodiments, the long-acting injectable formulations of the present invention may include one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the long-acting injectable formulations of the present invention may include an imidazothiazole compounds including, but not limited to, tetramisole, levamisole and butamisole. In still other embodiments, the long-acting formulations of the present invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the long-acting injectable formulations of the present invention may include the antinematodal compounds phenothiazine and piperazine as the neutral compound or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the long-acting injectable formulations of the present invention of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the long-acting formulations of the present invention of the invention including, but not limited to, arecoline in various salt forms, bunamidine, niclosamide, nitroscanate, paromomycin and paromomycin II.

In yet other embodiments, the long-acting injectable formulations of the present invention may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with an isoxazoline compounds in the long-acting formulations of the present invention can be a biologically active peptide or protein including, but not limited to, depsipeptides, which act at the neuromuscular junction by stimulating presynaptic receptors belonging to the secretin receptor family resulting in the paralysis and death of parasites. The depsipeptide may be a cyclic depsipeptide. In one embodiment of the depsipeptide, the depsipeptide is emodepside (see Willson et al., *Parasitology*, January 2003, 126(Pt 1):79-86). In another embodiment, the depsipeptide is PF1022A or a derivative thereof.

In another embodiment, the long-acting injectable formulations of the present invention may comprise an active agent from the neonicotinoid class of pesticides. The neonicotinoids bind and inhibit insect specific nicotinic acetylcholine receptors. In one embodiment, the neonicotinoid insecticidal agent that can be combined with an isoxazoline compound to form a long-acting injectable formulation of the invention is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health and the oral soft-chewable formulation Advantus™ from Piedmont Animal Health. Agents of this class are described, for example, in U.S. Pat. No. 4,742,060 or in EP 0 892 060.

In another embodiment, the long-acting injectable formulations of the present invention may comprise nitenpyram, another active agent of the neonicotinoid class of pesticides. Nitenpyram has the following chemical structure and is the active ingredient in the oral product CAPSTAR™ Tablets sold by Novartis Animal Health.

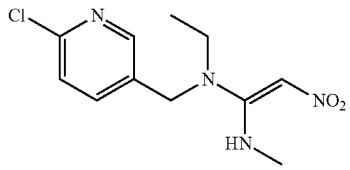 [SMILES: CCN(Cc1ccc(Cl)nc1)/C(=C/[N+](=O)[O-])NC]

Nitenpyram is active against adult fleas when given daily as an oral tablet. Nitenpyram works by interfering with normal nerve transmission and leads to the death of the insect. Nitenpyram has a very fast onset of action against fleas. For example, CAPSTAR™ Tablets begin to act against fleas in as early as 30 minutes after administration and is indicated for use as often as once a day. However, nitenpyram is only known to be effective when administered orally as a systemic parasiticide, as with CAPSTAR™ Tablets.

In yet another embodiment, the invention provides the long-acting formulations of the present invention comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula Ia) in combination with nitenpyram.

In yet another embodiment, the invention provides the long-acting formulations of the present invention comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula Ia) in combination with imidacloprid.

In certain embodiments, an insecticidal agent that can be combined with the long-acting formulations of the present invention is a semicarbazone, such as metaflumizone.

In another embodiment, the long-acting injectable formulations of the present invention may advantageously include a combination of isoxazoline compounds known in the art. These active agents are described in U.S. Pat. No. 7,964,204, US 2010/0254960 A1, US2011/0159107, US2012/0309620, US2012/0030841, US2010/0069247, WO 2007/125984, WO 2012/086462, U.S. Pat. Nos. 8,318,757, 8,466,115, 8,618,126, 8,822,466, 8,383,659, 8,853,186, US 2011/0144349, U.S. Pat. No. 8,053,452; US 2010/0137612, US 2010/0254959, US 2011/152081, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. Nos. 7,951, 828 & 7,662,972, US 2010/0137372 A1, US 2010/0179194 A2, US 2011/0086886 A2, US 2011/0059988 A1, US 2010/0179195 A1, U.S. Pat. Nos. 7,897,630, and 7,951,828, all of which are incorporated herein by reference in their entirety.

In another embodiment of the invention, nodulisporic acid and its derivatives (a class of known acaricidal, anthelmintic, anti-parasitic and insecticidal agents) may be added to the long-acting formulations of the present invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The formulations may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the. the long-acting formulations of the present invention These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181.

The compositions of the invention may also include aryloazol-2-yl cyanoethylamino compounds such as those described in U.S. Pat. No. 8,088,801 to Soll et al., which is incorporated herein in its entirety, and thioamide derivatives of these compounds, as described in U.S. Pat. No. 7,964, 621, which is incorporated herein by reference.

The long-acting injectable formulations of the present invention may also be combined with paraherquamide compounds and derivatives of these compounds, including derquantel (see Ostlind et al., Research in Veterinary Science, 1990, 48, 260-61; and Ostlind et al., *Medical and Veterinary*

*Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In another embodiment of the invention, the compositions may include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance*," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, the additional active agent is included in the long-acting formulations of the present invention in an amount of between about 0.1 µg and about 1000 mg. More typically, the additional active agent may be included in an amount of about 10 µg to about 500 mg, about 1 mg to about 300 mg, about 10 mg to about 200 mg or about 10 mg to about 100 mg.

In other embodiments of the invention, the additional active agent may be included in the composition to deliver a dose of about 5 µg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

The long-acting formulations of the present invention, which include at least an isoxazoline active agent, a poloxamer and a co-solvent, have been surprisingly discovered to be stable and effective against a broad spectrum of ectoparasites, and possibly also endoparasites if another active is included, for an extended period of time; e.g., a period from three (3) to six (6) months while exhibiting favorable properties with respect to the site of injection.

Poloxamers are a family of synthetic block copolymers of ethylene oxide and propylene oxide. Poloxamers may be liquid, a milky white paste or a powder and are represented by the following structure:

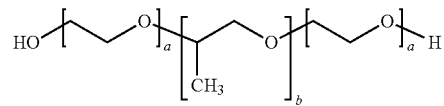

where a is an integer between 2 and 130 and b is an integer between 15 and 67 (see, U.S. Pat. No. 3,740,421). Poloxamer are available from commercial sources such as BASF and Croda. An example of a poloxamer is P-124 which is a solid at room temperature. In one embodiment, poloxamer P-124 has the values a=12 and b=20. Other poloxamers include P-128 (a=38 and b=29), P-181 (a=3 and b=30) P-188 (a=80 and b=27), P-237 (a=64 and b=37), P338 (a=141 and b=44) and P407 (a=101 and b=56).

Pharmaceutically acceptable polymers other than poloxamers are specifically excluded from the inventive long-acting formulations. For the purposes of this application, liquid polyethylene glycols, which function herein as co-solvents, are not defined as or considered to be a pharmaceutically acceptable polymers and, thus, their inclusion is permitted. Hence, the long-acting formulations of this invention provide for the inclusion of liquid polyethylene glycols. Examples of pharmaceutically acceptable polymers that are specifically excluded from the inventive long-acting formulations include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly (maleic anhydride), chitin, chitosan, and copolymers, terpolymers, or combinations or mixtures therein including copolymers of polylactides, polycaprolactones, polyglycolides (e.g., poly(lactide-co-glycolide)

The co-solvents used in the long-acting injectable compositions may be a single or a blend of co-solvents. In one embodiment, the co-solvents used in the long-acting injectable formulations of the present invention include polar solvents that are miscible in water. Non-limiting examples of these co-solvents include ethanol, isopropanol, benzyl alcohol, glycol ethers (e.g., including, but limited to, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), liquid polyethylene glycols (PEGs) (for example, PEG 400), propylene glycol, carbonates (e.g., propylene carbonate), 2-pyrrolidone, N-methylpyrrolidone, dimethyl isosorbide (DMI), Dimethylacetamide, glycerol formal or a mixture of at least two of these solvents.

In one embodiment, the long-acting formulations of the invention comprise a polar protic solvent including, but not limited to, an alcohol such as ethanol, isopropanol or a glycol or glycol ether.

In another embodiment, the long-acting injectable formulations of the invention comprise a polar aprotic solvent such as N-methylpyrrolidone, dimethyl isosorbide, dimethylacetamide or propylene carbonate.

In yet another embodiment of the invention, the compositions of the invention include non-water miscible co-solvents. Non-limiting examples of these co-solvents include triacetin, lipids, triglycerides including medium chain triglycerides such $C_8$-$C_{10}$ triglycerides such as capric/caprylic triglycerides, propylene glycol derivatives (e.g. propylene glycol monolaurate), caprylocaproyl polyoxyl-8 glycerides (Labrasol) (non-ionic water dispersible surfactant, isopropyl myristate, or a mixture of at least two of these co-solvents.

In one embodiment, the compositions include a protic solvent that is not completely miscible with water including, but not limited to, benzyl alcohol.

In another embodiment, the composition of the invention may include neutral oils as a co-solvent. Neutral oils are triglycerides of fractionated plant fatty acids with chain lengths of $C_8$ to $C_{10}$. Two commercially available products are known as MIGLYOL® 810 and MIGLYOL®812. In another embodiment, the neutral oil is a triglyceride of fractionated plant fatty acids with chain lengths of $C_8$ and $C_{10}$ combined with linoleic acid (about 4-5%). A commercially available product is known as MIGLYOL® 818. In yet another embodiment, the neutral oil is a glycerin ester of fractionated plant fatty acids with chain lengths of $C_8$ and $C_{10}$ combined with succinic acid. A commercially available product is known as MIGLYOL® 829. In another embodiment, the neutral oil may be a propylene glycol diester of saturated plant fatty acids with chain lengths of $C_8$ and $C_{10}$ combined with succinic acid. A commercially available product is known as MIGLYOL® 840 (propylene glycol dicaprylate/dicaprate). In yet another embodiment, the co-solvent may be a mixture of two or more neutral oils.

The inventive formulations may contain other inert ingredients such as antioxidants, preservatives, or pH stabilizers. These compounds are well known in the formulation art. Antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy anisole), BHT (butylated hydroxy toluene), BHA and citric acid, monothioglycerol, tert-butyl hydroquinone (TBHQ), and the like, may be added to the present formulation. The antioxidants are generally added to the formulation in amounts of from about 0.01 to about 2.0%, based upon total weight of the formulation, with about 0.05 to about 1.0% being especially preferred.

Preservatives, such as the parabens (methylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate.

Dosage forms may contain from about 0.5 mg to about 5 g of an active agent or a combination of active agents. More typically, the amount of active agent(s) in the compositions of the invention will be from about 1 mg to about 3 g. In another embodiment, the amount of active agent(s) in the compositions will be from about 20 mg to about 3 g. In another embodiment, the amount of active agent(s) present in the compositions will be from about 20 mg to about 2 g, about 20 mg to about 1.5 g or about 20 mg to about 1 g. In other embodiments, the amount of active agent(s) in the compositions will be from about 20 mg to about 500 mg, about 30 mg to about 200 mg or about 50 mg to about 200 mg. In still another embodiment, the amount of active agent(s) present in the compositions will be from about 50 mg to about 2 g, about 50 mg to about 1 g or about 50 mg to about 500 mg. In yet another embodiment of the invention, the about of active agent(s) present will be from about 100 mg to about 2 g, about 100 mg to about 1 g or about 100 mg to about 500 mg.

In another embodiment, the amount of active agent(s) present in an amount of from about 1 mg to about 500 mg of an active agent, about 1 mg to about 100 mg or about 1 mg to about 25 mg. In still other embodiments, the amount of the active agent present in the compositions is about 10 mg about 50 mg or about 10 mg to about 100 mg. In other embodiments, the amount of active agent present in the compositions is about 50 mg to about 200 mg, about 100 mg to about 300 mg, about 100 mg to about 400 mg, about 200 mg to about 500 mg, about 300 mg to about 600 mg, about 400 mg to about 800 mg, or about 500 mg to about 1000 mg.

The compositions of the invention are made by mixing the appropriate amount of the active agents, a poloxamer, a co-solvent and, optionally, an antioxidant, pharmaceutically acceptable additive and/or excipient to form a formulation of the invention. In some embodiments the formulations of the present invention can be obtained by following the method of making these forms described above by the description of making these forms found in general formulation text known to those in the art, e.g. *Remington—The Science and Practice of Pharmacy* ($21^{st}$ *Edition*) (2005), *Goodman & Gilman's The Pharmacological Basis of Therapeutics* ($11^{th}$ *Edition*) (2005) and *Ansel's Pharmaceutical Dosage Forms and Drug Delivery Systems* ($8^{th}$ *Edition*), edited by Allen et al., Lippincott Williams & Wilkins, (2005).

Methods of Treatment

In another aspect of the invention, a method for preventing or treating a parasite infestation/infection in an animal is provided, comprising administering to the animal a long-acting injectable formulation comprising an effective amount of at least one isoxazoline compound, a poloxamer and a co-solvent. The formulations of the invention have long-lasting efficacy against ectoparasites (e.g. fleas and ticks) and in certain embodiments may also be active against endoparasites that harm animals.

In one embodiment of the invention, methods for the treatment or prevention of a parasitic infestation or infection in a domestic animal are provided, which comprise administering a long-acting injectable formulation comprising an effective amount of at least one isoxazoline active agent to the animal. Ectoparasites against which the methods and compositions of the invention are effective include, but are not limited to, fleas, ticks, mites, mosquitoes, flies and lice.

In certain embodiments wherein the inventive formulations include one or more additional active agents that are active against internal parasites the compositions and methods of the invention may also be effective against endoparasites including, but not limited to, cestodes, nematodes, hookworms and roundworms of the digestive tract of animals and humans.

In one embodiment for treatment against ectoparasites, the ectoparasite is one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include, but are not limited to, cat and dog fleas (*Ctenocephalides felis, Ctenocephalides* sp. and the like), ticks (*Rhipicephalus* sp., *Ixodes* sp., *Dermacentor* sp., *Amblyomma* sp. and the like), and mites (*Demodex* sp., *Sarcoptes* sp., *Otodectes* sp. and the like), lice (*Trichodectes* sp., *Cheyletiella* sp., *Linognathus* sp., and the like), mosquitoes (*Aedes* sp., *Culex* sp., *Anopheles* sp., and the like) and flies (*Haematobia* sp. including *Haematobia irritans, Musca* sp., *Stomoxys* sp. including *Stomoxys calcitrans, Dermatobia* sp., *Cochliomyia* sp., and the like).

Additional examples of ectoparasites include but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vituli*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In some embodiments of the invention, the composition can also be used to treat against endoparasites such as those helminths selected from the group consisting of *Anaplocephala, Ancylostoma, Necator, Ascaris, Capillaria, Cooperia, Dipylidium, Dirofilaria, Echinococcus, Enterobius, Fasciola, Haemonchus, Oesophagostomum, Ostertagia, Toxocara, Strongyloides, Toxascaris, Trichinella, Trichuris,* and *Trichostrongylus*, among others.

In one embodiment, the invention provides methods for the treatment and prevention of parasitic infections and infestations of animals (either wild or domesticated), including livestock and companion animals such as cats, dogs, horses, birds including chickens, sheep, goats, pigs, deer, turkeys and cattle, with the aim of ridding these hosts of parasites commonly encountered by such animals.

In an embodiment, the invention provides methods and compositions for the treatment or prevention of parasitic infections and infestations in companion animals including, but not limited to, cats and dogs. The methods and compositions are particularly effective for preventing or treating parasitic infestations of cats and dogs with fleas and ticks.

In another embodiment, the methods and compositions of the invention are used for the treatment or prevention of parasitic infections and infestations in cattle or sheep. When treating livestock animals such as cattle or sheep, the methods and compositions are particularly effective against *Rhipicephalus (Boophilus) microplus, Haematobia irritans* (horn fly), *Stomoxys calcitrans* (stable fly), and sheep myiasis such as *Lucilia sericata, Lucilia cuprina* (known as blowfly strike in Australia, New Zealand and South Africa).

The terms "treating" or "treat" or "treatment" are intended to mean the administration of a long-acting formulation of the present invention to an animal that has a parasitic infestation for the eradication of the parasite or the reduction of the number of the parasites infesting the animal undergoing treatment. It is noted that the compositions of the invention may be used to prevent such a parasitic infestation.

The terms "prevent", "prevention" or "prophylaxis" are intended to mean the administration of the long-acting formulations of the present invention to the animal before the parasitic infection or infestation has occurred in order to keep said infection or infestation from occurring.

The formulations of the invention are administered in parasiticidally effective amounts which are which are suitable to control the parasite in question to the desired extent, as described below. In each aspect of the invention, the compounds and compositions of the invention can be applied against a single pest or combinations thereof.

By "antiparasitic effective amount" is intended a sufficient amount of a composition of the invention to eradicate or reduce the number of parasites infesting the animal. In some embodiments, an effective amount of the active agent achieves at least 70% efficacy against the target parasite compared to an untreated control. In other embodiments, an effective amount of the active agent achieves at least 80%, or at least 90% efficacy against the target pests. Preferably, an effective amount of the active agent will achieve at least 95%, at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In some embodiments for companion animals, the dose of the isoxazoline active agent administered from the topical compositions of the invention is between about 0.1 to about 50 mg per kg of body weight. More typically the dose of the isoxazoline active agent administered is about 0.5 to about 30 mg/kg or about 0.5 to about 30 mg/kg body weight. In another embodiment, the dose of the isoxazoline active agent administered is about 10 to about 30 mg/kg, about 15 to about 30 mg/kg or about 20 to about 30 mg/kg of body weight.

In other embodiments, the dose administered may be lower depending on the animal and the isoxazoline administered. For example, if the composition comprises the more active enantiomer of the isoxazoline compounds a lower dose may be administered. In some embodiments, the dose is from about 0.1 to about 30 mg/kg of body weight. In another embodiment, the dose may be from about 0.1 to about 20 mg/kg or about 0.1 to about 10 mg/kg of body weight. In other embodiments, the dose may be from about 1 to about 20 mg/kg of body weight or about 1 to about 10 mg/kg. In yet another embodiment, the dose may be from about 5 to about 20 mg/kg or about 10 to about 20 mg/kg of body weight.

In other embodiments for the treatment of livestock animals such as cattle or sheep, doses of the isoxazoline active agent administered may be about 0.1 to about 40 mg/kg of body weight. More typically the doses administered will be about 1 to about 30 mg/kg, about 1 to about 20 mg/kg or about 1 to about 10 mg/kg of bodyweight. In yet another embodiment, the dose may be from about 10 to about 25 mg/kg, about 15 to about 30 mg/kg of body weight or about 20-30 mg/kg of body weight.

In one embodiment of the method of use in dogs or cats, the long-acting formulations of the present invention comprising an isoxazoline compound has an efficacy against fleas and/or ticks of at least about 90.0% or higher for about 3 months, or longer, compared with a non-treated control. In another embodiment, the long-acting formulations of the present invention provide an efficacy against fleas and/or ticks of at least 95.0% or higher for about, 3 months or longer. In another embodiment, the long-acting formulations of the present invention provide an efficacy against fleas and/or ticks of at least 90.0% or higher for about, 4 months or longer. In yet another embodiment, the long-acting formulations of the present invention provide an efficacy against fleas and/or ticks of at least 95.0% or higher for about, 4 months or longer. In another embodiment, the long-acting formulations of the present invention provide an efficacy against fleas and/or ticks of at least 90.0% or higher for about, 5 months or longer. In yet another embodiment, the long-acting formulations of the present invention provide an efficacy against fleas and/or ticks of at least 95.0% or higher for about, 5 months or longer.

In another embodiment, the long-acting formulations of the present invention provide an efficacy against fleas and/or ticks on cats and dogs of at least about 80% for two months, or longer. In another embodiment, the long-acting formulations of the present invention provide an efficacy against fleas and/or ticks on cats and dogs of about 90% for about 3 months, or longer. In still another embodiment, the compositions provide an efficacy against fleas and/or ticks on cats and dogs of about 95% for about 3 months or longer. In yet another embodiment, the long-acting formulations of the present invention provide an efficacy against fleas and/or ticks on cats and dogs of at least 90% or higher for about, 4 months or longer. In yet another embodiment, the long-acting formulations of the present invention provide an efficacy against fleas and/or ticks on cats and dogs of at least 95% or higher for about, 4 months or longer. In another embodiment, the long-acting formulations of the present invention provide an efficacy against fleas and/or ticks on cats and dogs of at least 90% or higher for about, 5 months or longer. In yet another embodiment, the long-acting formulations of the present invention provide an efficacy against fleas and/or ticks on cats and dogs of at least 95% or higher for about, 5 months or longer.

In another embodiment, the long-acting formulations of the present invention has an efficacy of at least about 80% against fleas and/or ticks for about 3 months, or longer. In still another embodiment, the long-acting formulations of the invention provide an efficacy of at least about 90% against fleas and/or ticks for 3 months or longer. In yet another embodiment, the long-acting formulations of the present invention of the invention provide an efficacy of at least about 95% against fleas and/or ticks for 3 months or longer. In still another embodiment, the long-acting formulations of the present invention provide an efficacy against fleas and/or ticks in cats and/or dogs of at least 80% or at least 90% for about 3 months to about 6 months or longer.

In still another embodiment, the long-acting formulations of the present invention provide an efficacy against fleas and/or ticks in cats and/or dogs of at least 80% or at least 90% for about 7 months, 8 months, 9 months or longer.

In another aspect of the invention, a kit for the treatment or prevention of a parasitic infestation in an animal is provided, which comprises a long-acting formulation of the invention and a syringe.

EXAMPLES

The invention is further described by the following non-limiting examples which further illustrate the invention, and are not intended, nor should they be interpreted to, limit the scope of the invention.

Formulation Examples

The following long-acting injectable formulations were prepared by mixing the following ingredients:

Example 1

| | |
|---|---|
| Compound of formula (Ia) | 30% (w/v) |
| Ethanol | 9% (w/v) |
| Poloxamer 124 | QS. |

Example 2

| | |
|---|---|
| Compound of formula (Ia) | 15% (w/w) |
| Poloxamer 124 | 85% (w/w) |

Example 3

| | |
|---|---|
| Compound of formula (Ia) | 26% (w/w) |
| Poloxamer 124 | 10% (w/w) |
| PEG 400 | 64% (w/w) |

Example 5

| | |
|---|---|
| Compound of formula (Ia) | 26% (w/w) |
| Poloxamer 124 | 66% (w/w) |
| Ethanol | 8% (w/w) |

Example 6

| | |
|---|---|
| Compound of formula (Ia) | 26% (w/w) |
| PEG 400 | 27% (w/w) |
| Poloxamer 181 | 39% (w/w) |
| Ethanol | 8% (w/w) |

Example 7

| Compound of formula (Ia) | 26% (w/w) |
|---|---|
| PEG 400 | 64% (w/w) |
| Poloxamer 181 | 10% (w/w) |

Example 9

| Compound of formula (Ia) | 26% (w/w) |
|---|---|
| Poloxamer 124 | 63.4% (w/w) |
| Capryol 90 | 10.6% (w/w) |

Example 10

| Compound of formula (Ia) | 26% (w/w) |
|---|---|
| Poloxamer 124 | 66% (w/w) |
| Benzyl alcohol | 8% (w/w) |

Example 11

| Compound of formula (Ia) | 15% (w/w) |
|---|---|
| Poloxamer 124 | 85% (w/w) |

Example 12

| Compound of formula (Ia) | 26% (w/w) |
|---|---|
| Poloxomer 181 | 10% (w/w) |
| PEG 400 | 64% (w/w) |

Example 13

| Compound of formula (Ia) | 26% |
|---|---|
| PEG 400 | 33% (w/w) |
| Poloxomer 124 | 33% (w/w) |
| Ethanol | 8% (w/w) |

Example 14

| Compound of formula(S)-(Ia) | 13% (w/w) |
|---|---|
| PEG 400 | 39.5% (w/w) |
| Poloxamer 124 | 39.5% (w/w) |
| Ethanol | 8% (w/w) |

Example 15

| Compound of formula (Ia) | 26% (w/w) |
|---|---|
| PEG 400 | 33% (w/w) |
| Poloxomer 181 | 33% (w/w) |
| Ethanol | 8% (w/w) |

Example 16

| Compound of formula (S)-(Ia) | 13% (w/w) |
|---|---|
| PEG 400 | 39.5% (w/w) |
| Poloxomer 181 | 39.5% (w/w) |
| Ethanol | 8% (w/w) |

Example 17

| Compound of formula (S)-(Ia) | 13% (w/w) |
|---|---|
| PEG 400 | 27% (w/w) |
| Poloxomer 124 | 52% (w/w) |
| Ethanol | 8% (w/w) |

Example 18

| Compound of formula(S)-(Ia) | 26% (w/w) |
|---|---|
| PEG 400 | 52% (w/w) |
| Poloxomer 124 | 14% (w/w) |
| Ethanol | 8% (w/w) |

Example 19

| Compound of formula (S)-(Ia) | 26% (w/w) |
|---|---|
| PEG 400 | 33% (w/w) |
| Poloxomer 124 | 33% (w/w) |
| Ethanol | 8% (w/w) |

Efficacy Examples

The following examples demonstrate the efficacy of the long-acting injectable compositions of the invention against ectoparasites in companion and farm animals.

Example 20

An efficacy study was run to determine the efficacy of the formula in Example 1 dosed at 20 mg/kg in beagles against *Rhipicephalus sanguineus* (tick) and *Ctenocephalides felis* (flea). Compared with a non-treated control, the efficacy against ticks on Day 184 48 hours after infestation was 74%. On day 185, 72 hours after infestation, efficacy against ticks was 90.4%. Efficacy against fleas on Day 193, 24 hours after infestation, was 85.6%.

Example 21

The efficacy of a long-acting injectable composition of the invention against *Rhipicephalus (Boophilus) microplus* in cattle was tested. Two groups of cattle were studied, a non-treated control group and a test group treated with a long-acting injectable of the invention comprising 15% (w/v) of Formula Ia in a carrier comprising a mixture of poloxomer 124 (QS) and 20% (w/v) ethanol to deliver a dose of 5 mg/kg of body weight. Cattle in the treatment group were treated on Day 0 with the long-acting injectable composition. Each animal was infested with 5000 tick larvae on days 7, 21, and every 14 days thereafter. Adult ticks dropping from each animal are collected daily from Day 1 until the end of the study. The efficacy of the treatment is determined by collecting and counting the number of ticks dropping from each animal and comparing with the number of ticks collected from the control group. The efficacy of the long-acting composition was found to be about almost 100% for infestations conducted on day 7, 21, 35, and 49; 95% at for infestations conducted at Day 63; and greater than 70% at for infestations conducted at Day 91.

Injection Site Irritation

Example 22

The following example accessed the irritation of the long-acting injectable compositions of the invention (compositions of Treatment Groups Nos. 2-6) in beagle dogs against a placebo (Treatment Group No. 1).

The compositions of the following Treatment Groups in Table 1 were prepared:

TABLE 1

| Group | Compound of Formula (Ia) | Compound of Formula (S)-(Ia) | Poloxomer 124 | PEG 400 | Ethanol | Dose (mg/kg) | Dose volume (ml/kg) |
| --- | --- | --- | --- | --- | --- | --- | --- |
| 1 | — | — | 46 | 46 | 8 | N/A | 0.08 |
| 2 | 13 | — | 39.5 | 39.5 | 8 | 12.5 | 0.08 |
| 3 | — | 13 | 39.5 | 39.5 | 8 | 12.5 | 0.08 |
| 4 | 26 | — | 33 | 33 | 8 | 12.5 | 0.04 |
| 5 | 26 | — | 52 | 14 | 8 | 12.5 | 0.04 |
| 6 | 13 | — | 52 | 27 | 8 | 12.5 | 0.08 |

All concentrations are in % w/w.

A composition from each of the Treatment Groups was subcutaneously injected into a dog at two sites and the irritation at the two injection sites was monitored for 1 or two weeks respectively and assessed according to the following criteria:

0 no detectable reaction
1 thickening of injection site, no distinct nodule (non-fluctuant).
2 small (pea size) nodule≤approximately 0.5-2 cm in diameter
3 medium (grape size) nodule>approximately 2-3 cm in diameter
4 large (walnut size) nodule>3 cm in diameter
5 abscess formation Criteria # a lower score is deemed a better result (e.g. 0-2 vs. 3-5).

Table 2 provides the assessment of the above-identified groups at the first injection site on the indicated day post injection.

TABLE 2

| Group | Day 1 | Day 3 | Day 7 | Day 10 | Day 14 |
| --- | --- | --- | --- | --- | --- |
| 1 | 0 | 0 | 0 | 0 | 0 |
| 2 | 0 | 0 | 0 | 0 | 0 |
| 3 | 0 | 0 | 0 | 0 | 2 |
| 4 | 0 | 0 | 0 | 2 | 0 |
| 5 | 0 | 0 | 0 | 0 | 0 |
| 6 | 0 | 0 | 0 | 0 | 0 |

Table 3 provides the assessment for the above-identified Treatment Groups at the second injection site at the indicated day post injection.

TABLE 3

| Group | Day 3 | Day 7 |
| --- | --- | --- |
| 1 | 0 | 0 |
| 2 | 0 | 0 |
| 3 | 0 | 0 |
| 4 | 0 | 0 |
| 5 | 0 | 0 |
| 6 | 0 | 0 |

The data in Table 1 and 2 indicate that the inventive formulations exhibited either no or very minor irritation at the injection site and the injection site irritation was comparable to the placebo, which did not contain an isoxazoline active agent.

Efficacy and Injection Site Irritation Site Evaluation.

Example 23

The efficacy and the injection site irritation of a long-acting injectable composition according to the invention (Treatment Group 5) was compared against placebo compositions (Treatment Groups 1 and 2) and an injectable composition comprising a PEG 400/ethanol (80:20 (v/v)) co-solvent mixture (Treatment Group 3). Eight dogs were evaluated in each of the treatment groups. The long-acting injectable compositions were administered on day 0.

The compositions of the following Treatment Groups in Table 4 were prepared

TABLE 4

| Group | Compound of Formula (Ia) (% w/v) | Poloxomer 124 (% v/v) | PEG 400 (% v/v) | Ethanol (% v/v) | Dose (mg/kg) | Dose volume (ml/kg) |
|---|---|---|---|---|---|---|
| 1 | — | — | 80 | 20 | N/A | 0.067 |
| 2 | — | 80 | — | 20 | N/A | 0.067 |
| 3 | 30 | — | QS (80:20 PEG400/EtOH) | QS (80:20 PEG400/EtOH) | 15 | 0.05 |
| 4 | 30 | — | QS (80:20 PEG400/EtOH) | QS (80:20 PEG400/EtOH) | 20 | 0.067 |
| 5 | 30 | QS | — | 20 | 20 | 0.067 |

Site Irritation

The compositions from Treatment Groups 1-5 were subcutaneously injected to beagle dogs at Day 0 to assess the injection site irritation for the compositions described in Table 5—

TABLE 5

| Group | Days 0-3 | Day 7 | Day 14 | Day 28 |
|---|---|---|---|---|
| 1 | 0 (4 dogs) | 0 (4 dogs) | 0 (4 dogs) | 0 (4 dogs) |
| 2 | 0 (4 dogs) | 0 (4 dogs) | 0 (4 dogs) | 0 (4 dogs) |
| 3 | 0 (8 dogs) | 1 (8 dogs) | 2 (2 dogs) 3 (3 dogs) 3 (3 dogs) | 0 (8 dogs) |
| 4 | 0 (8 dogs) | 1 (8 dogs) | 1 (6 dogs) 3 (2 dogs) | 0 (8 dogs) |
| 5 | 0 (8 dogs) | 0 (8 dogs) | 0 (5 dogs) 2 (2 dogs) 2 (1 dogs) | 0 (8 dogs) |

The following criteria were used to evaluate the injection site irritation:

0 no detectable reaction 1 thickening of injection site, no distinct nodule (non-fluctuant).

2 small (pea size nodule)≤approximately 0.5-2 cm in diameter 3 medium (grape size) nodule>approximately 2-3 cm in diameter 4 large (walnut size) nodule>3 cm in diameter 5 abscess formation Criteria A lower score is deemed a better result (e.g. 0-2 vs. 3-5). The number of dogs assigned a given score is listed parentheses.

Efficacy Vs. *Rhipicephalus sanguineus* (Ticks) and *Ctenocephalides felis* (Fleas).

Dogs from Treatment Groups 3, 4 and 5 were infested with 50 *Rhipicephalus sanguineus* on Day 182. Thumb counts were performed on Day 184 and tick removal and counting on Day 185.

Dogs were infested with 100 *Ctenocephalides felis* on Day 192. Fleas were removed and counted on Day 193. Overall the data demonstrates that the inventive compositions showed good bioavailability, close to 6 month flea and tick efficacy, and minimal injection site reactions.

The invention is further described in the following numbered paragraphs:

1. A long-acting injectable formulation for the treatment or prevention of parasite infestations or infections in an animal comprising an antiparasitic effective amount of at least one isoxazoline active agent, a poloxamer and, optionally, a co-solvent, wherein no other pharmaceutically acceptable polymers are present.

2. The long-acting injectable formulation according to paragraph 1 comprising:

a) an antiparasitic effective amount of at least one isoxazoline active agent, which is:

i) an isoxoazoline compound of formula (I):

(I)

wherein:

$A^1, A^2, A^3, A^4, A^5$ and $A^6$ are independently selected from the group consisting of $CR^3$ and N, provided that at most 3 of $A^1, A^2, A^3, A^4, A^5$ and $A^6$ are N;

$B^1, B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —NO$_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, OR$^{10}$, NR$^{11}$R$^{12}$ or Q$^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2; or a pharmaceutically acceptable salt thereof; and/or ii) an isoxazoline compound of formula (II):

(II)

wherein:

$R_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$A_1$ is oxygen; and $A_2$ is oxygen, $NR_2$ or $CR_7R_8$;

G is G-1 or G-2;

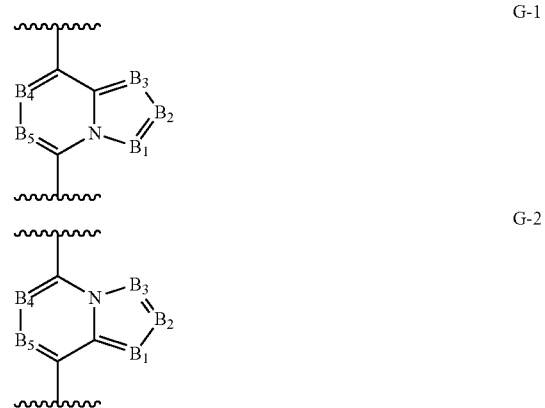

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl) amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, R—$C(O)NR_8$—, —CN or —$NO_2$; or Y is Y-1, Y-2, Y-3, Y-4, Y-5, Y-6, Y-7, Y-8, Y-9, Y-10, Y-11, Y-12 or Y-13;

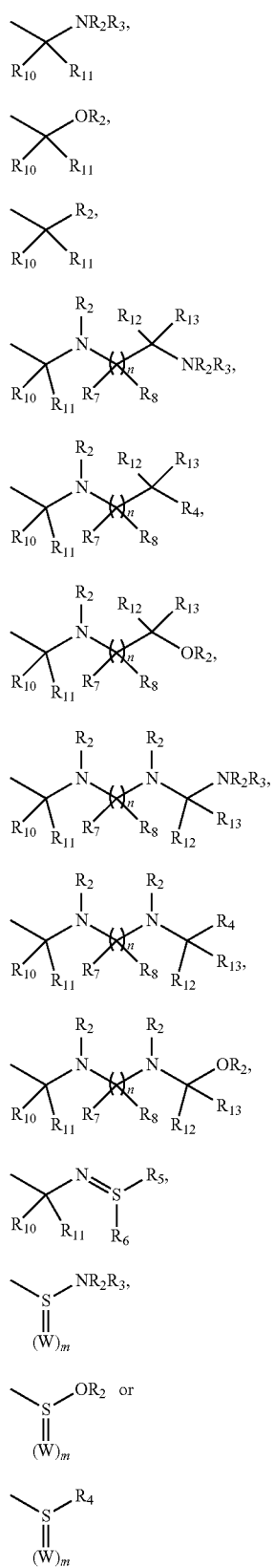

R$_2$, R$_3$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, R$_{10}$S(O)—, R$_{10}$S(O)$_2$—, R$_{10}$C(O)—, R$_{10}$C(S)—, R$_{10}$R$_{11}$NC(O)—, R$_{10}$R$_{11}$NC(S)— R$_{10}$OC(O)—;

R$_4$, R$_5$ and R$_6$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl or heteroaryl;

R$_7$ and R$_8$ are independently hydrogen, alkyl, haloalkyl, thioalkyl, alkylthioalkyl, hydroxyalkyl, alkoxylakyl, alkenyl, haloalkenyl, alkynyl or haloalkynyl;

R$_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—, —CN or —NO$_2$;

R$_{10}$, R$_{11}$, R$_{12}$ and R$_{13}$ are each independently hydrogen, alkyl, haloalkyl, thioalkyl, alkylthioalkyl, hydroxyalkyl, alkoxylakyl, alkenyl, haloalkenyl, alkynyl or haloalkynyl; or R$_{10}$ together with R$_{11}$ form =O, =S or =NR$_2$; or R$_{12}$ together with R$_{13}$ form =O, =S or =NR$_2$;

W is O, S or NR$_2$;

n is 1-4; and m is 0, 1 or 2; or a pharmaceutically acceptable salt thereof; and/or iv) an isoxoazoline compound of formula (III)

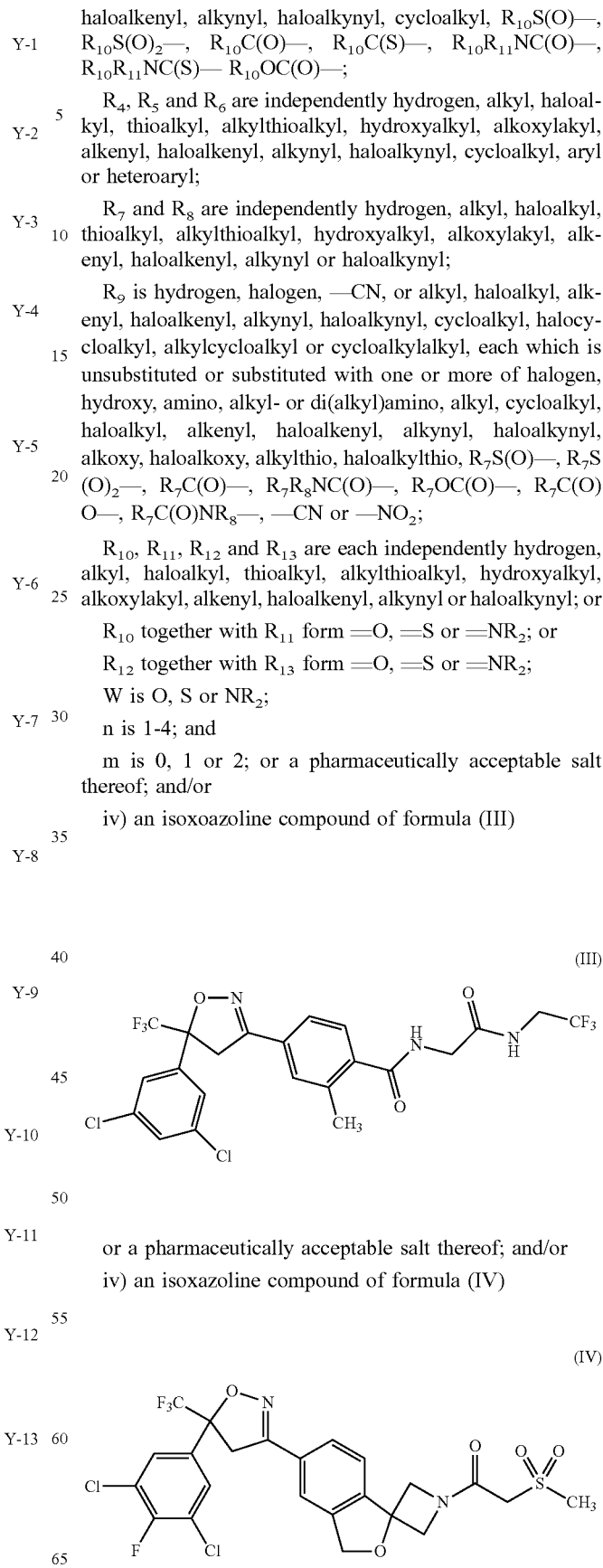

or a pharmaceutically acceptable salt thereof; and/or iv) an isoxazoline compound of formula (IV)

or a pharmaceutically acceptable salt thereof; and/or v) a isoxazoline compound of formula (V):

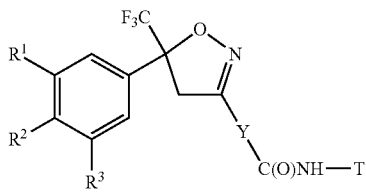

wherein $R^1$, $R^2$ and $R^3$ are independently H, $C_1$, F or $CF_3$;
Y is the diradical group

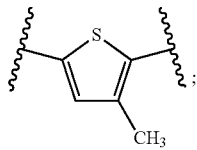

and

T is a $C_1$-$C_6$-alkyl group which is unsubstituted or substituted by halogen, cyano, nitro, amino, hydroxyl, $C_1$-$C_6$-alkoxy, $C_1$-$C_6$-haloalkoxy, $C_1$-$C_6$-alkylthio, $C_1$-$C_6$-alkylthio, carboxy, carbamoyl or $C_2$-$C_6$-alkanoyl group which may be unsubstituted or substituted in the alkyl portion by halogen or a pharmaceutical acceptable salt thereof; and/or vi) an isoxazoline compound of formula (VI):

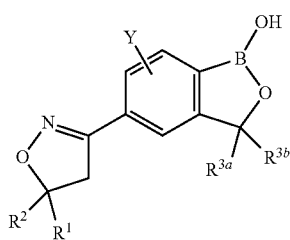

wherein Y is hydrogen, fluoro, chloro or bromo;
$R^1$ is phenyl substituted with 2-4 substituents selected from halogen, methyl, difluoromethyl, trifluoromethyl, methoxy, trifluoromethoxy or trifluoroethoxy;
$R^2$ is methyl, fluoromethyl, trifluoromethyl or perfluoroethyl;
$R^{3a}$ and $R^{3b}$ are independently selected from hydrogen, methyl, ethyl or fluoromethyl; or $R^{3a}$ and $R^{3b}$ together combine with the carbon to which they are attached to form a cyclopentyl ring or a cyclohexyl ring; or a pharmaceutically acceptable salt thereof;

b) at least one pharmaceutically acceptable polymer which is a poloxamer;

c) optionally, at least one co-solvent;

d) optionally, an antioxidant; and e) optionally at least one pharmaceutically acceptable additive, excipient or mixtures thereof
wherein no other pharmaceutically acceptable polymers are present.

3. The long-acting injectable formulation according to paragraph 2 comprising:

a) an antiparasitic effective amount of at least one isoxazoline compound of formula (I):

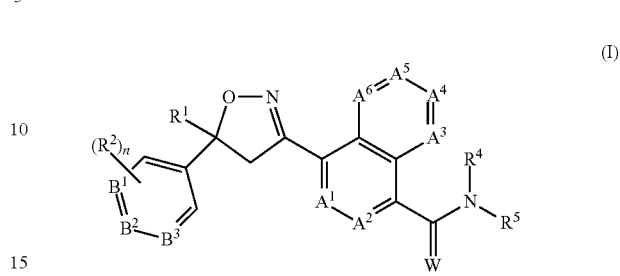

wherein:

$A^1$, $A^2$, $A^3$, $A^4$, $A^5$ and $A^6$ are independently selected from the group consisting of $CR^3$ and N, provided that at most 3 of $A^1$, $A^2$, $A^3$, $A^4$, $A^5$ and $A^6$ are N;

$B^1$, $B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2;

or a pharmaceutically acceptable salt thereof;

b) at least one pharmaceutically acceptable polymer which is a poloxamer;

c) optionally, at least one co-solvent;

d) optionally, an antioxidant; and e) optionally at least one pharmaceutically acceptable additive, excipient or mixtures thereof wherein no other pharmaceutically acceptable polymers are present.

4. The long-acting injectable formulation according to paragraph 3, wherein in the isoxazoline active agent is a compound of the formula

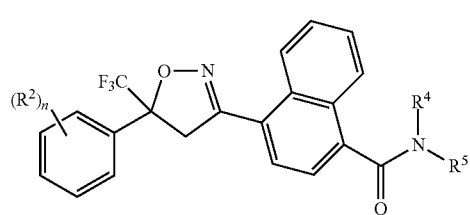

(Ib)

or a pharmaceutically acceptable salt thereof.

wherein $R^2$ independently is halogen, $C_1$-$C_6$ alkyl or $C_1$-$C_6$ haloalkyl $R^4$ is H or $C_1$-$C_6$ alkyl;

$R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl; and n is 0, 1 or 2.

5. The long-acting injectable formulation according to paragraph 4, wherein in the isoxazoline active agent is a compound of formula (Ia):

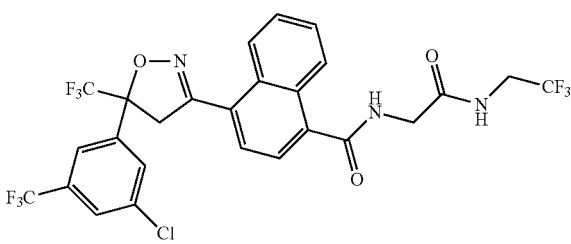

(Ia)

or a pharmaceutically acceptable salt thereof.

6. The long-acting injectable formulation according to paragraph 1 or 2, wherein the isoxazoline active agent is enriched in an enantiomer.

7. The long-acting injectable formulation according to paragraph 6, wherein in the isoxazoline active agent is enriched in a compound of formula (S)-(Ia) or (R)-(Ia):

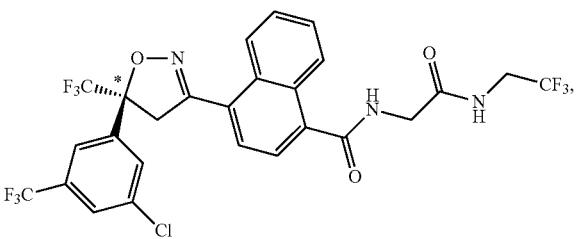

(S)-(Ia)

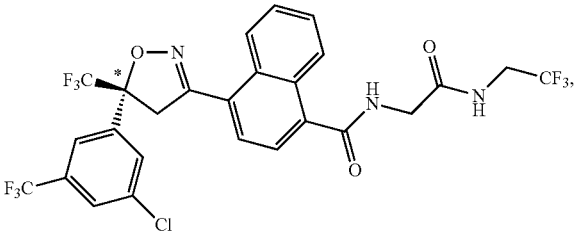

(R)-(Ia)

or a pharmaceutically acceptable salt thereof.

8. The long-acting injectable formulation according to paragraph 2 comprising:

a) an antiparasitic effective amount of at least one isoxazoline compound of formula (II):

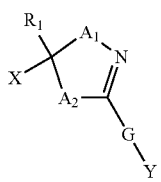
(II)

wherein:

$R_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;

$A_1$ is oxygen; and
$A_2$ is oxygen, $NR_2$ or $CR_7R_8$;
G is G-1 or G-2;

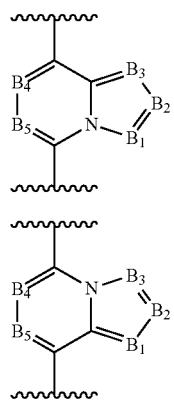

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$; or Y is Y-1, Y-2, Y-3, Y-4, Y-5, Y-6, Y-7, Y-8, Y-9, Y-10, Y-11, Y-12 or Y-13;

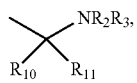
Y-1

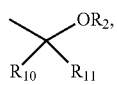
Y-2

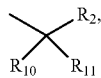
Y-3

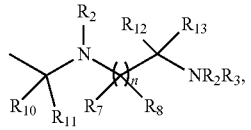
Y-4

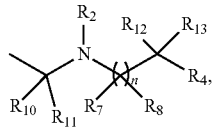
Y-5

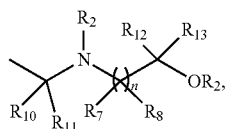
Y-6

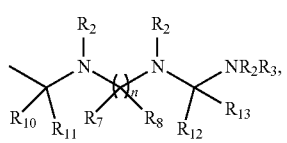
Y-7

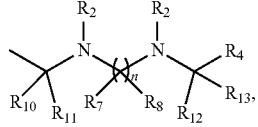
Y-8

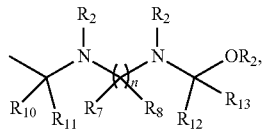
Y-9

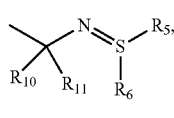
Y-10

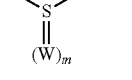
Y-11

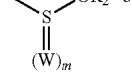
Y-12 or

Y-13

$R_2$, $R_3$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, $R_{10}S(O)—$, $R_{10}S(O)_2—$, $R_{10}C(O)—$, $R_{10}C(S)—$, $R_{10}R_{11}NC(O)—$, $R_{10}R_{11}NC(S)—$ $R_{10}OC(O)—$;

$R_4$, $R_5$ and $R_6$ are independently hydrogen, alkyl, haloalkyl, thioalkyl, alkylthioalkyl, hydroxyalkyl, alkoxylakyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxylakyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)—$, $R_7S(O)_2—$, $R_7C(O)—$, $R_7R_8NC(O)—$, $R_7OC(O)—$, $R_7C(O)O—$, $R_7C(O)NR_8—$, —CN or —NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxylakyl, alkenyl, haloalkenyl, alkynyl or haloalkynyl; or $R_{10}$ together with $R_{11}$ form =O, =S or =NR_2$; or
$R_{12}$ together with $R_{13}$ form =O, =S or =NR_2$;
W is O, S or $NR_2$;
n is 1-4; and
m is 0, 1 or 2; or a pharmaceutically acceptable salt thereof, b) at least one pharmaceutically acceptable polymer which is a poloxamer;
c) optionally, at least one co-solvent;
d) optionally, an antioxidant; and
e) optionally, at least one pharmaceutically acceptable additive, excipient or mixtures thereof
wherein no other pharmaceutically acceptable polymers are present.

9. The long-acting injectable formulation according to paragraph 8 wherein isoxazoline agent is a compound of formulae II-1.001 to II-1.025 or 11-2.00-11-2.018:

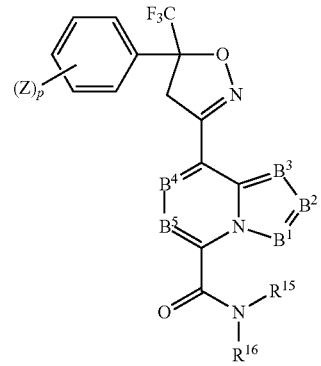

Compounds II-1.001 to II-1.025

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 1.001 | 3,5-Cl_2 | C—H | C—H | C—H | C—H | N | H | $CH_2C(O)NHCH_2CF_3$ |
| 1.002 | 3,5-Cl_2 | C—H | C—H | C—H | C—H | N | H | $CH_2CF_3$ |
| 1.003 | 3,5-(CF_3)_2 | C—H | C—H | C—H | C—H | N | $CH_3$ | $CH_2CO_2CH_3$ |
| 1.004 | 3,5-(CF_3)_2 | C—H | C—H | C—H | C—H | N | $CH_3$ | $CH_2CO_2H$ |
| 1.005 | 3,5-(CF_3)_2 | C—H | C—H | C—H | C—H | N | $CH_3$ | $CH_2C(O)NHCH_2CF_3$ |
| 1.006 | 3,5-(CF_3)_2 | C—H | C—H | C—H | C—H | N | H | $CH_2C(O)NHCH_2CF_3$ |
| 1.007 | 3,5-(CF_3)_2 | C—H | C—H | C—H | C—H | N | H | $CH_2CH_2SCH_3$ |
| 1.008 | 3,5-(CF_3)_2 | C—H | C—H | C—H | C—H | C—H | H | $CH_2C(O)NHCH_2CF_3$ |
| 1.009 | 3,5-(CF_3)_2 | C—H | C—H | C—H | C—H | C—H | H | $CH_2CH_2SCH_3$ |
| 1.010 | 3,5-(CF_3)_2 | C—H | C—H | C—H | C—H | C—H | H | $CH_2CF_3$ |
| 1.011 | 3,5-Cl_2 | C—H | C—H | C—H | C—H | C—H | H | $CH_2C(O)NHCH_2CF_3$ |
| 1.012 | 3,5-Cl_2 | C—H | C—H | C—H | C—H | C—H | H | $CH_2CF_3$ |
| 1.013 | 3,5-Cl_2 | C—H | C—H | C—H | C—H | C—H | H | $CH_2CH_2SCH_3$ |
| 1.014 | 3-Cl,5-CF_3 | C—H | C—H | C—H | C—H | C—H | H | $CH_2C(O)NHCH_2CF_3$ |
| 1.015 | 3-Cl,5-CF_3 | C—H | C—H | C—H | C—H | C—H | H | $CH_2CF_3$ |
| 1.016 | 3-Cl,5-CF_3 | C—H | C—H | C—H | C—H | C—H | H | $CH_2CH_2SCH_3$ |
| 1.017 | 3,5-Cl_2 | C—H | C—H | C—Me | C—H | C—Me | H | $CH_2C(O)NHCH_2CF_3$ |
| 1.018 | 3,5-Cl_2 | C—H | C—H | C—Me | C—H | C—Me | H | $CH_2CF_3$ |
| 1.019 | 3,5-Cl_2 | C—H | C—H | C—Me | C—H | C—Me | H | $CH_2CH_2SCH_3$ |
| 1.020 | 3,5-(CF_3)_2 | C—H | C—H | C—Me | C—H | C—Me | H | $CH_2C(O)NHCH_2CF_3$ |
| 1.021 | 3,5-(CF_3)_2 | C—H | C—H | C—Me | C—H | C—Me | H | $CH_2CF_3$ |
| 1.022 | 3,5-(CF_3)_2 | C—H | C—H | C—Me | C—H | C—Me | H | $CH_2CH_2SCH_3$ |
| 1.023 | 3-Cl,5-CF_3 | C—H | C—H | C—Me | C—H | C—Me | H | $CH_2C(O)NHCH_2CF_3$ |
| 1.024 | 3-Cl,5-CF_3 | C—H | C—H | C—Me | C—H | C—Me | H | $CH_2CF_3$ |
| 1.025 | 3-Cl,5-CF_3 | C—H | C—H | C—Me | C—H | C—Me | H | $CH_2CH_2SCH_3$ |

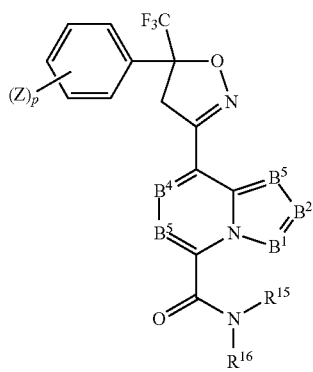

Compounds II-2.001 to II-2.018

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 2.001 | 3,5-Cl$_2$ | C—H | C—H | N | C—H | C—H | H | CH$_2$C(O)NHCH$_2$CF$_3$ |
| 2.002 | 3,5-Cl$_2$ | C—H | C—H | N | C—H | C—H | H | CH$_2$CF$_3$ |
| 2.003 | 3,5-Cl$_2$ | C—H | C—H | N | C—H | C—H | H | CH$_2$CH$_2$SCH$_3$ |
| 2.004 | 3,5-(CF$_3$)$_2$ | C—H | C—H | N | C—H | C—H | H | CH$_2$C(O)NHCH$_2$CF$_3$ |
| 2.005 | 3,5-(CF$_3$)$_2$ | C—H | C—H | N | C—H | C—H | H | CH$_2$CF$_3$ |
| 2.006 | 3,5-(CF$_3$)$_2$ | C—H | C—H | N | C—H | C—H | H | CH$_2$CH$_2$SCH$_3$ |
| 2.007 | 3-Cl,5-CF$_3$ | C—H | C—H | N | C—H | C—H | H | CH$_2$C(O)NHCH$_2$CF$_3$ |
| 2.008 | 3-Cl,5-CF$_3$ | C—H | C—H | N | C—H | C—H | H | CH$_2$CF$_3$ |
| 2.009 | 3-Cl,5-CF$_3$ | C—H | C—H | N | C—H | C—H | H | CH$_2$CH$_2$SCH$_3$ |
| 2.010 | 3,5-Cl$_2$ | C—H | C—H | C—H | C—H | C—H | H | CH$_2$C(O)NHCH$_2$CF$_3$ |
| 2.011 | 3,5-Cl$_2$ | C—H | C—H | C—H | C—H | C—H | H | CH$_2$CF$_3$ |
| 2.012 | 3,5-Cl$_2$ | C—H | C—H | C—H | C—H | C—H | H | CH$_2$CH$_2$SCH$_3$ |
| 2.013 | 3,5-(CF$_3$)$_2$ | C—H | C—H | C—H | C—H | C—H | H | CH$_2$C(O)NHCH$_2$CF$_3$ |
| 2.014 | 3,5-(CF$_3$)$_2$ | C—H | C—H | C—H | C—H | C—H | H | CH$_2$CF$_3$ |
| 2.015 | 3,5-(CF$_3$)$_2$ | C—H | C—H | C—H | C—H | C—H | H | CH$_2$CH$_2$SCH$_3$ |
| 2.016 | 3-Cl,5-CF$_3$ | C—H | C—H | C—H | C—H | C—H | H | CH$_2$C(O)NHCH$_2$CF$_3$ |
| 2.017 | 3-Cl,5-CF$_3$ | C—H | C—H | C—H | C—H | C—H | H | CH$_2$CF$_3$ |
| 2.018 | 3-Cl,5-CF$_3$ | C—H | C—H | C—H | C—H | C—H | H | CH$_2$CH$_2$SCH$_3$ | or a pharmaceutically acceptable salt thereof.

10. The long-acting injectable formulation according to paragraph 2 wherein isoxazoline active agent is a compound of formula (III):

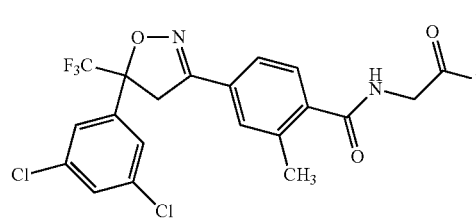

or a pharmaceutically acceptable salt thereof.

11. The long-acting injectable formulation according to paragraph 2, wherein isoxazoline compound is a compound of formula (IV):

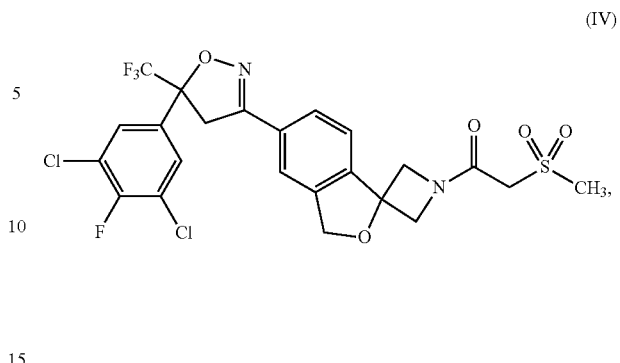

or a pharmaceutically acceptable salt thereof.

12. The long-acting injectable formulation according to paragraph 2, wherein the isoxazoline compound is a compound of formula (Va):

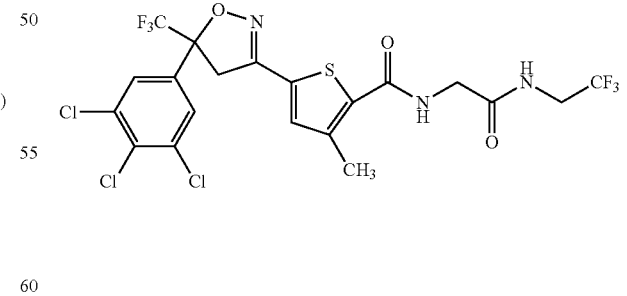

or a pharmaceutically acceptable salt thereof.

13. The long-acting injectable formulation according to paragraph 2, wherein the isoxazoline compound is a compound of formula (VIa):

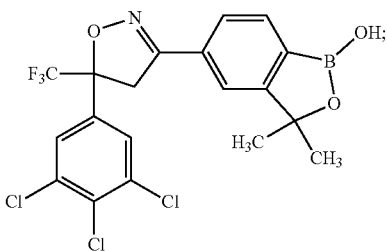

or a pharmaceutically acceptable salt thereof.

14. The long-acting injectable formulation according to paragraph 1, wherein the poloxamer is poloxamer 124 or poloxamer P-181, P-188, P-237, P338 or P407.

15. The long-acting injectable formulation according to paragraph 1, wherein the co-solvent is methanol, ethanol, isopropanol, benzyl alcohol or a liquid polyethylene glycol.

16. The long-acting injectable composition according to paragraph 1 comprising:
a) about 5 to 30% (w/v) of an isoxazoline compounds of Formula (I):

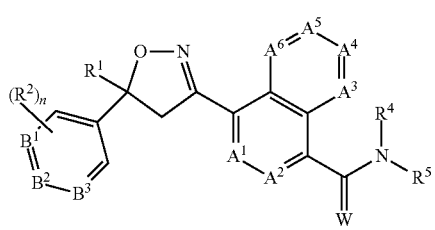

wherein:
$A^1, A^2, A^3, A^4, A^5$ and $A^6$ are independently selected from the group consisting of $CR^3$ and N, provided that at most 3 of $A^1, A^2, A^3, A^4, A^5$ and $A^6$ are N;

$B^1$, $B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2 or a pharmaceutically acceptable salt thereof;

b) pharmaceutically acceptable polymer which is a poloxamer;

c) optionally, about 5% to 40% (w/v) of co-solvent selected from the group consisting of liquid polyethylene glycol, ethanol and isopropanol;

d) optionally, about 0.01% to about 2.0% (w/v) of an antioxidant; and e) optionally about 0.01% to about 5.0% (w/v) of a pharmaceutically acceptable additive, excipient or mixtures thereof wherein the only pharmaceutically acceptable polymer present in said long-acting injectable composition is a poloxamer and wherein the poloxamer is present in the overall composition in a proportion representing the complement to 100% of the composition.

17. The long-acting injectable formulation according to paragraph 1 wherein the formulation treats or prevents parasites for about 3 to 6 months.

18. The long-acting injectable formulation according to paragraph 1 wherein the formulation treats or prevents parasites for about 5 to 6 months.

19. The long-acting injectable formulation according to paragraph 1 wherein the formulation treats or prevents parasites for about 6 months.

20. The long-acting injectable formulation according to paragraph 1 wherein the formulation treats or prevents parasites for about 7 months.

21. The long-acting injectable formulation according to any one of paragraphs 17, 18 or 19 wherein the parasites are fleas or ticks 22. The long-acting injectable formulation according to paragraph 1 comprising:

a) about 5 to 30% (w/v) of an isoxazoline active compound of formula (Ia)

(Ia)

or a pharmaceutically acceptable salt thereof, b) pharmaceutically acceptable polymer which is a poloxamer;

c) optionally, about 5% to 40% (w/v) of co-solvent selected from the group consisting of liquid polyethylene glycol, ethanol and isopropanol;

d) optionally, about 0.01% to about 2.0% (w/v) of an antioxidant; and e) optionally, about 0.01% to about 5.0% (w/v) of a pharmaceutically acceptable additive, excipient or mixtures thereof;

wherein the only pharmaceutically acceptable polymer present in said long-acting injectable composition is a poloxamer and wherein the poloxamer is present in the overall composition in a proportion representing the complement to 100% of the composition.

23. The long-acting injectable formulation according to paragraph 19, wherein the isooxazoline compound is:

(S)-Ia or a pharmaceutically acceptable salt thereof.

24. The long-acting formulation according to any one of paragraphs 1-23, which further comprise an effective amount at least one additional pharmaceutically active agent.

25. The long-acting formulation according to paragraph 24, wherein the additional pharmaceutically active agent is a macrocyclic lactone.

26. The long-acting formulation according to paragraph 25, wherein the macrocyclic lactone is abamectin, dimadectin, doramectin, emamectin, eprinomectin, ivermectin, latidectin, lepimectin, selamectin, ML-1,694,554, milbemectin, milbemycin D, moxidectin or nemadectin.

27. A method for treating or preventing parasites in an animal in need thereof for a period of 3 to 6 months which comprises administering the long acting injectable formulation according to paragraph 1 to said animal.

28. The method according to paragraph 27 wherein the animal is a dog, cat, sheep or cattle.

29. The method according to paragraph 27 wherein the parasites are treated or prevented for about 5 to 6 months 30. The method according to paragraph 27 wherein the parasites are treated or prevented for about 6 months 31. The method according to paragraph 27 wherein the parasites are fleas and/or ticks.

32. The use of an isoxazoline in the preparation of a long-acting injectable formulation for the treatment or prevention of a parasite infestation or infection on or in an animal.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A long-acting injectable formulation for the treatment of parasite infestations or infections in an animal comprising:

a) an antiparasitic effective amount of at least one isoxazoline active agent of formula (Ib):

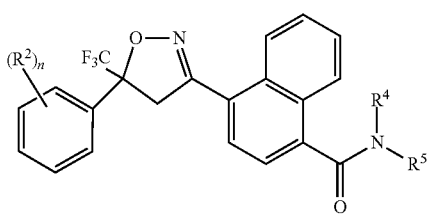

(Ib)

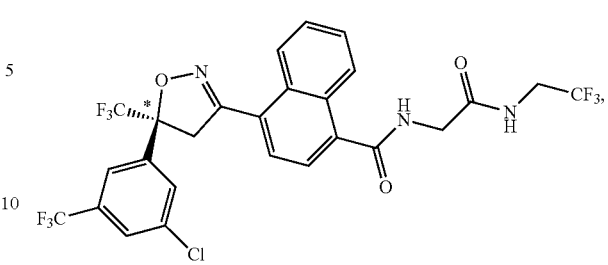

(S)-(Ia)

or a pharmaceutically acceptable salt thereof
wherein:
$R^2$ independently is halogen, $C_1$-$C_6$ alkyl or $C_1$-$C_6$ haloalkyl;
$R^4$ is H or $C_1$-$C_6$ alkyl;
$R^5$ is $C_1$-$C_4$ alkyl optionally substituted with one or more $R^7$;
$R^7$ is independently halogen, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl; and
n is 0, 1 or 2;
b) poloxamer 124 or poloxamer 181;
c) a co-solvent selected from the group consisting of liquid polyethylene glycol, ethanol, isopropanol, and a mixture thereof;
d) optionally, an antioxidant; and
e) optionally at least one pharmaceutically acceptable additive, excipient or mixtures thereof;
wherein the only pharmaceutically acceptable polymers present in said long-acting injectable formulation is said poloxamer, wherein the formulation treats parasitic infestations or infections for about 3 to 6 months.

2. The long-acting injectable formulation according to claim 1, wherein the at least one isoxazoline active agent is a compound of formula (Ia):

(Ia)

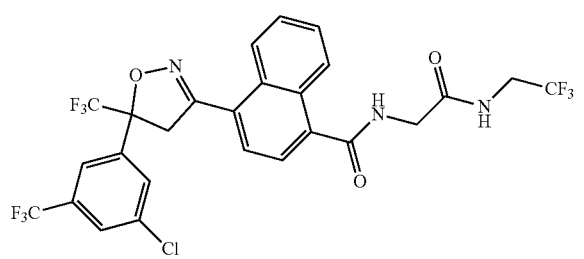

or a pharmaceutically acceptable salt thereof.

3. The long-acting injectable formulation according to claim 1, wherein the at least one isoxazoline active agent is enriched in an enantiomer.

4. The long-acting injectable formulation according to claim 3, wherein the at least one isoxazoline active agent is enriched in a compound of formula (S)-(Ia):

or a pharmaceutically acceptable salt thereof.

5. The long-acting injectable formulation according to claim 1 wherein the formulation treats parasite infestations or infections for about 5 to 6 months.

6. The long-acting injectable formulation according to claim 1 wherein the formulation treats parasite infestations or infections for about 6 months.

7. The long-acting injectable formulation according to any one of claims 5 or 6, wherein the parasites are fleas or ticks.

8. The long-acting injectable formulation according to claim 1 comprising:
   a) about 5 to 30% (w/v) of the at least one isoxazoline active compound of formula (Ib) or a pharmaceutically acceptable salt thereof,
   b) poloxamer 124 or poloxamer 181;
   c) about 5% to 40% (w/v) of co-solvent selected from the group consisting of liquid polyethylene glycol, ethanol, isopropanol, and a mixture thereof;
   d) optionally, about 0.01% to about 2.0% (w/v) of an antioxidant; and
   e) optionally, about 0.01% to about 5.0% (w/v) of a pharmaceutically acceptable additive,
   excipient or mixtures thereof;
   wherein the only pharmaceutically acceptable polymer present in said long-acting injectable composition is said poloxamer and wherein the poloxamer is present in the overall composition in a proportion representing the complement to 100% of the composition.

9. The long-acting injectable formulation according to claim 8, wherein the at least one isoxazoline active agent is:

(S)-(Ia)

or a pharmaceutically acceptable salt thereof.

10. The long-acting formulation according to claim 1, which further comprises an effective amount at least one additional pharmaceutically active agent.

11. The long-acting formulation according to claim 10, wherein the at least one additional pharmaceutically active agent is a macrocyclic lactone.

12. The long-acting formulation according to claim 11, wherein the macrocyclic lactone is abamectin, dimadectin, doramectin, emamectin, eprinomectin, ivermectin, latidectin, lepimectin, selamectin, ML-1,694,554, milbemectin, milbemycin D, moxidectin or nemadectin.

13. A method for treating a parasitic infection or infestation in an animal in need thereof for a period of 3 to 6 months which comprises administering the long acting injectable formulation according to any one of claim 1, 2-4, or 8-12 to said animal.

14. The method according to claim 13 wherein the animal is a dog, cat, sheep or cattle.

15. The method according to claim 13 wherein the parasites are treated for about 5 to 6 months.

16. The method according to claim 13 wherein the parasites are treated for about 6 months.

17. The method according to claim 13 wherein the parasites are fleas and/or ticks.

\* \* \* \* \*